(12) United States Patent
Khatib

(10) Patent No.: US 9,322,068 B2
(45) Date of Patent: Apr. 26, 2016

(54) METHODS AND COMPOSITIONS FOR IMPROVED FERTILIZATION AND EMBRYONIC SURVIVAL

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/309,868

(22) Filed: Jun. 19, 2014

(65) Prior Publication Data

US 2014/0330071 A1    Nov. 6, 2014

Related U.S. Application Data

(62) Division of application No. 13/563,750, filed on Aug. 1, 2012, now Pat. No. 8,790,875.

(60) Provisional application No. 61/514,030, filed on Aug. 2, 2011.

(51) Int. Cl.
*C12Q 1/68* (2006.01)
*A61D 19/02* (2006.01)
*A61D 19/04* (2006.01)

(52) U.S. Cl.
CPC .............. *C12Q 1/6888* (2013.01); *A61D 19/02* (2013.01); *A61D 19/04* (2013.01); *C12Q 1/6876* (2013.01); *C12Q 2600/124* (2013.01); *C12Q 2600/156* (2013.01)

(58) Field of Classification Search
CPC ...... A61D 19/02; A61D 19/04; C12Q 1/6876; C12Q 1/6888; C12Q 2600/124; C12Q 2600/156
See application file for complete search history.

(56) References Cited

U.S. PATENT DOCUMENTS 8,790,875 B2 *   7/2014   Khatib ................. C12Q 1/6876
                                                435/6.1

OTHER PUBLICATIONS

Zhang B. et al. J. Dairy Sci. (2011) 94 :4174-4182.*

* cited by examiner

*Primary Examiner* — Stephen Kapushoc
(74) *Attorney, Agent, or Firm* — Kening Li; Miller Canfield

(57) ABSTRACT

Single nucleotide polymorphic sites of the bovine HSP genes are associated with improved fertilization rate and/or improved embryo survival rate in cattle. Nucleic acid molecules, kits, methods of genotyping and marker assisted bovine breeding methods based on these SNPs are disclosed.

16 Claims, 7 Drawing Sheets

```
83821 tagcaattca gatcttgatg tgaaaatgtc agtgatctcc tcaagggtgg aaagctaact
83881 atagctcctt gagcgccacc cttccattgc tgattcattt cctgcttccc ttttccttct
83941 caaatgggtg gtgtgatatc agtaaaaggc ccagataaag tcaggacagt gcatacgcca
84001 ctgctgtcta gatgttttgt gtgtgtgtgt ggtttgttgt gagccactca ggtcttaaga
84061 tgttttcaac agctgtggat catttgtact caaggggagg aataaaaaat aaaaaacaaa
84121 cacagagact ggtgagctgg actgttagct tgagtgctaa gcatgaaagt gttcaggact
84181 agaagttaga aggtgtatga tgcttaaata tttttagtgt gacagtttgg ggccagtatt
84241 tttatatgta agggagctcc tgtttgtcat ttttaacgat tctgaatttg aaattcacct
84301 cagttttcct ctggttcttt acgttagaaa taattcattg tgaagaatta tgaaaactga
84361 cttcatttta tttaaggcgc agtgacgctg tctgtgctcc ataagtattc tgatggcact
84421 gtgtcagaga gcaggggca tacccttaa cgttatttt attatcactg attttttatc
84481 atattattta ctaatattga ccaatattag tgaaatgctt ttagagctga gtagtatata
84541 gttgcctttt taacttattt ttatgaaaat gtatggtttg ataaaacttt gaaggcaccc
84601 ttggattgct tcacctcctt cagaaagata acttccttca tagaagaatg ttctttcctt
                                                              (DNAJC15-6F)
84661 aaaacaaac agaaaaaatt acgtcttgga gaaggactgt tatttatttt acctaa
84721                    tctg gtcagatatt tggcatttga aaggtaatgt ctgaccagtg
84781 aaatgtttga gtgtgtttta aattactcct gatcataagt ttattttct cagagattat
84841 cctgactgt taggtatctg tagtgcttca ttgaacgagt ttaacttata ctgttgtgat
84901 ttctagagag cttataaat aatttgtcag ggcatgaatg tgtgggaaaa tatcagagac
84961 atctaactga gtgttttct ttatttgaga cttaaaaa tgtcagtagt gaagtgtcct
85021 ttaatccatt tctctttctt tgtcctctca ggtgggtctc cttacttagc aaccaaaatt
85081 aatgaagcaa aagacctgct agaagcaacc accaaacact gatggacgct caaggaccac
85141 tctgaggag aagaagggg gccttataaa agctgtcctg cacattagtc taaacgtgg
85201 cattcacaat ttcatatgtg caccgaccac agccatttct tccgtgtctg agctatgtga
85261 taataaaga tgaacagtct agctttgtat tggctttcag aggagcacat ggaa
         (DNAJC15-6R)
85321                    ctca tttcttcct ctctctgata gtcatacatt tgaagacttc
85381 tactactaag ttccccccgac cccagccct gcagcagtat cattatcagt aatataattg
85441 gaatttgggca gcaagagtgt agaattttt gctgcttata tttatgctcg cattgtccct
85501 tgtttcttca aaggaattta gcactctgcc tatgtgaagt gctttaaatg ttatgagacg
85561 aaaccctgac tgccacccca ggaaagtgaa ctgaagcttg atggaattta ctaaagggtg
85621 ttttgtaaag cagtggttag gaaagaacgc tgctctccca gagatcccaa ggctgtagca
85681 tgagaacttg gagagctgct aaaatgatta aaggtttaca gaatgagccc tgtgaggaaa
85741 gcctggaaat tgctgggaga agtctgaggg attcgtactt aattatatag tcttctggtg
85801 ctgtgtactt attcaattat gcattctaca aatatttatt taccacctgt agcgggtgag
85861 gtactgtagg ggtcctcagg agttccaggt gtgaaccagg cacggatcgt gacccaaagg
85921 aacttgaatt tagagaaag ataaaccaca ggagtactat tagagaggca cagatgatag
85981 gcaaagaagt tcaaaataaa agactatttt cactgggca tcaggggggc gtgtcataga
86041 atcagtagcg tagagctggg ctttaaaaac aatgagatat accatatgat gggtgagtca
86101 gaattagcag aaatagggta tattagttca ttggagtgca gggtttctcc aaagtaacgg
86181 atgaacacac agtctggaag ggctggccct gtaatgtgca gtgcattcaa ttatttttt
86221 tttcccctc aacacagccc ctggttatca tcacttttct aaaagggaga aaagagagag
86281 tcagaatacc agcatatttc ttgtactgct ttacgacgct gggctcatcc caggtaaaca
86341 gaactaccac gtttcatctg tcttaaacgc tcttgtaata gtctagaggc atctttcatt
86401 ttacgacatc ctgtagttgg gagttctcag cattggtgat actgactcat tgagctgctg
86461 attcctgctt gtgggggct ctcctgtgta tggtaggatg attagcaaca tccctgcctg
86521 cacctacgaa aggccaggag cgcccctct gttgtgcaa ccgaaaatgt atctagatgt
86581 tgccaaacgt tccttggagg gcaaaattgc cccagtaga gagccactgc tctaaatgtt
86641 aacccgtgttc tcctttggta catgaaataa tggatggcct gacttgaaat tgattcttag
86701 gttcactgaa atacggctct cgctttaaaa tccctgtgt gtcacagttt tttgtgcttt
86761 agtatgtttt ctggcccact gctgcccgg taccttaagt gccctcctga tacccagatc
86821 tccacgtgtt caaagcctgg ggatagttga aggccaagct gaaaagtctg tctctccttt
86881 tctggtgctt ccagcaaaag taatcccatg aattgtcagc tctcagcaaa caaggattgt
86941 atcgtcttg gtcactgcta cattgacact caataaatat ttgttaaatg aacgaataca
87001 ttcccgtagc actttattct tcacatttgg taacttgtga aacaactctt tgtgtgacat
87061 gacttatttc ttctacaaaa gtacaagaac ctttagagca agaatcttgt catttgtctt
87121 tgtaacctcc ttaagagtgg agcactgggg actttgtaga catcataaag ttgtaagtac
87181 taaaaaaaat gtttttgaa tactatgctt caaaaaatgt aaccactagt tttgaaagtt
```

Figure 1

```
87241 atgttatgca atattggggt accctcagaa catacctgtt agttgacatc attttctagt
87301 ccacactgtg ttcatgaaaa tttaagtcct cagcactagc ttgaaatttc cttcattcta
87361 ttctcattta tctgttgagt gtgtgcccaa aaatcagaca cctggtttta agtactatcc
87421 tcctatcaca taatctgggg caattaatct gcaaggcttt aattgcctca tctataaaat
87481 agagaaaata ataaccctat ctaaaaaggt ccatctagtc aaggctatgg tttttccagt
87541 ggtcatgtat ggatgtgaga gttggactgt gaagaaggct gagcgccgaa gaattgatgc
87601 ttttgaactg tggtgttgga gaagactctt gagagtccct tggactgcaa ggacatccaa
87661 ccagtccatc ctaaaggaga tcagtcctgg gtgttcattg gagggactga tgctgaagct
87721 gaaactccaa tactttggcc acctcatgcg aagagctgac tcattggaaa agaccctgat
87781 gctgggaggg gttgggggca ggaggagaag gggacgacag aggatgagat ggctggatgg
87841 catcaccaac tcgatggatg tgagtttggg taagctccgg gagttggtgc tggacaggga
87901 ggcctggcat gctgcgattc atggggttgc aaagagtcgg acacgactga gtgactgaac
87961 tgaactgaaa aaggttgtt
```

Figure 1 (continued)

```
34081 ttgctcagtt gtgcccgact ctttgcaacc ccatggactg tagcctacta ggttccttgc
34141 tccatgggat tctccaggca agagtaccac agtgggttgc catttccttc tccagaggat
34201 cttcctgacc cagggatcga acccaggtct cccgcattcc aggcagacac tttaacctct
34261 gagccactag ggatgggaag agggagacag ttattggtca cccttgattt gacaagcgtt
34321 actgaggatg ctttaaacac ctgacgaaat tcagtgacc ttgtagcgta aagttaattg
34381 gtggcttttg gggcttccca ggtggcacag tggtaaagaa tctgcctgcc catgcaagag
34441 atgcaagaga cttgggttcg atccctgggt ggggaagatc tctgaagaa gggaatggcc
34501 acccactcca gtattcttgc ctggagaatt ccatggacag aggagcctgg tgggctacag
34561 gccatagggt tgcaaagagt cgggcacaac tgagcaacta atattacttt tactattgta
34621 tatccaaattc agcttttttg ttgttttgtc ctttcccta tggaccctgc tccctggctg
34681 actttgtccg ctgtttgctt ctggaactac atgccgtgtc tctgttccct ctctggcctc
34741 tgccatttct ttccctgcgg ctctgtgttt cccatcaccg gatcaattcc tgaaacccat
34801 cttcttgcag agtcctcctc caggggggcc ttgccctgat ggctcttgt cctcatcgct
34861 tccatcagca attatttgct gagtgccaaa tgcctgtgag gcgctaacca ctaattttca
34921 gttgattatg tttgtatact cactttgtat tgtctgtttt tctacttgaa tgttacatat
34981 tatttgtcca ttgtttgttt cccagtcctt tagtctaacc tttgagaaag ggtcacgata
35041 atttcagata tgcttac##############cca ggcagctgaa atgcagtgga
35101 cagagggtgg ggctgaccct cctactgaca tagagctctg cttttcttt gcagggatga
35161 agtcaataaa gcatatcgga agcttgctgt gctgcttcac cctgacaaat gtgtagcacc
35221 tggtagtgaa gatgccttca aagccgttgt gaatgcccga acagccctcc tgaaaaacat
35281 caagtagaaa ataggaaaaa aagacaggtg taggcctcga gtccaaacag actttctctg
35341 gaagtaaaat agccaacatg ggttttttcct ccacaaaatt cttacagccc ttttcactca
35401 cgtgctgtca ttgtgaatc agtaatttgg ctgcctgttt ccatgtcaca gacatttgc
35461 agagagacaa aatgaagaga accgagtgcc acttatacac tgtcgttcat tttctatttc
35521 tgaatgatga tagattttt tttttttctc atgagttggt aagctgtcgg tatagcatca
35581 cttgggcact ttgctcagga aagtccacaa agtttctgga agaaggatag gaggatcctt
35641 ttgcttttc ttattaaaa aaacattcat catcagagga aaaaaaaaca aaatggaag
35701 cag####################ggt gactttacaa gcaagttgcc cctttacaat
35761 gagtttctaa ggtgatattt taagcatcag tctgcttaat taatgaatga actcttggca
35821 gcccttcgga agtgaaacaa ggtgatgcta tcctgagctg agtggccctt ttttgacgtt
35881 cggtctgtgc cccttctcca tcaccggggg agagaccagc cagtcctgag agtagaggtg
35941 gcggtagccg caggttctgg tagactggct gctgctagac ctgccctgg gtctgaggcc
36001 tttccctggc cgtgggagtg ctggtagctg taggggcatc ttcacctagg agtctggagt
36061 cagatcccaa gacacaaatg cctgcaggtc aaactggatt gtgtacacat tcccagaggg
36121 cctgacccgc ctggttcggg cgtgtctgat gccctaggag agcccccata ggaggcttat
36181 gcc####################t########################gcaggg ttgcgtctca
36241 acagggggcc tcccttcgct tcctcgtcag tgtgagctcc cctccctct tctgttcctg
36301 ccttgtctct caaggcaccg catctgccac cacgtctctc ttctcgaatc cccaccttcc
36361 ggctattgcc tcctctgtcc tgtgcagcct ttgctgggc ctggtagacc agagacaagt
36421 atagatcctt ggggtggtgg atggagagat cttaaggcct gtgtgggaag aatttgttac
36481 ttttgtttag gttccaaatt tctgatcagt aatacttta agctgcagat tatgaaaatt
36541 aatttcacat agagaaatcc attctcttgc tatcgtctgt ctctcagtat ccaagagatg
36601 gatgaagatc aagtgtcagg accggcttc cttccagagc tcacagaata gagtcaccac
36661 gtggcgtgtt acaccatcac tctcacgtta ctcagattgt tagctgtgac caagctgcac
36721 taattggggc tttaaagtat atgaagcttt gccatcagtg aatttaagc agctatccca
36781 tattgattgc caagtag##################ga agaaaaacca ctttcattta
36841 attcaaaccc actgcagctt actgaaccct tcccttctcc agagcagctt cgctttgtgt
36901 ggctactctt ggcagcact gagctggttg tcaggaaacc agagcattgt tttctagtaa
36961 gagttttcat tttgatatta aaaatgcttt ttttttcttag taaaattgag atatgagata
37021 tgattttttg tgggatttc ctcttgcctt ttaatttaa ctagcttctg ggcctgtaaa
37081 actcaggcca aagttcttca gggttttaat tttgctgttg gccttcatca tggccaaagt
37141 aacaaacata gatctgttct tgtggcagaa cttaagagtc acatgagtga ggaactgtgc
37201 atggtggtgt cagcccacat tgacatgaca gctcacttgt gtatgtggcc ctgtgtaaaa
37261 actggtgcca gttttcatca ctgtcattaa acactagatg ggtcacctca ttcagctaca
37321 ttgtgcagat gagcagttat agcagataga gttctctagt tcttccattc acatccttat
37381 gtaatgagtg acttgttgac atttagcctg gtcttgatt################cat
37441 #caccttga ttactaatgt taaggatggc catgtactac ttcatttatg gaaagaaag
37501 aaaagaaaga taaaggttca gggtcctaga attttctga tttccataat cctgagtaga
37561 atgtcaagaa gtaatgaaat gaagcctgat ctgcaatgaa aagtaacttc atataaaatt
```

Figure 2

```
37621 ttacagacct ctgtgcatta atttaaattc ttggtacaaa tgtatatttt ttagttcaac
37681 cttattaaaa ttcttcagcc agttaggatt gcacaataca tcagtgagag taacaactag
37741 cagaataatt tcaatggcta aaaaaaattt tatacagaat cttgtttttt caaaaaagaa
37801 caagaagttt gaacagctgt tattcaagaa aagccatttc ttgggcatct gagtcaccaa
37861 gaatgaacac tttaaaaact tgttagaaat ccctggaggt ttttgaaatt aatcgccaac
37921 ctacctaaga acttaaaaat ataccatcct tttgttcctc ccttcctctt tcatggctcc
37981 ttttgaatca atattctcaa ctgtcaacgt gtctcttact tcagcaatgt cgtttatttc
38041 tttgcatgaa tgtgtgcttg gtaaagt░░░░░░░░░░░░░░░░░░░░░░░░ttcccaaga
38101 taaattgctc tgattctgta gattgcactc tgtgctttaa ggctcacatt tacctcagga
38161 aactcacttt agtatgtttt gttttgtttt gggttttttt gcattgaatt ctcaaatggt
38221 aattatttct ttatactggt aaactagtac ctaatttact gttcactaag tgagccatag
38281 ataaggcagc taaatttctg aaagaaagaa aaaataggca gcccttgatt gctgtgaatc
38341 agtaataagg tccctatttc tcaagagca atgacagaat ctcaagggga aggaggtatt
38401 tcggtctcat gttagaaagg ggggggggttg tgcacattgc ctttgacagg ░░░░░░░░░░
38461 ░░░░░░░░░░gcaatttca gtgggcccta gaatgtcact cccttctcta ctacactctg
38521 tctagctcac tctgagtctg actacatttt tgtgaaactt ttgcagagaa attaagccgc
38581 aaaatggagc taacctcctt ccattgcaag ttttgc░░░░░░░░░░░░░░░░░░░░░tttc
38641 tcatgatagg tacctagcac aattgtaaga gacagttact aatgtttata tgttggtgtt
38701 tccattaagc atttctagag gagacgaaag cttaaacttg tggtgtggat gagttagatc
38761 gtgtctgaca agcagtgcaa tatgaagctg tgcaataaag gctgtgttgt gaaatgaagc
38821 actggaaagc tggacagttc gggttagctt cctgcagcaa ttgcccgcag gatggtctgc
38881 ccttggccca ggaatgcaaa gaaacccttt gctcttacga ggtaatttat gtatttgctt
38941 tctgttgaaa taatggaaaa tgttaaagct aacagctgtc tatgtcttgt atagagagtg
39001 tcatatgtat ttaagttgtg tattttata aagtaaagcc aaatgccaaa tactggtctg
39061 tgggctgcac tcatttgttg agacactggc ctttgaagca gaagctggcc g░░░░░░░░░
39121 ░░░░░░░░░taagacatc ttgctttagt tgccagtggg taaaatgaag gaaatggtat
39181 tcagtggtcc ctcaggctgt tctaaccta attaagttgt gatgaaagtc tctgctctct
39241 taaagaaaga tactaatatt atgtttgcct ttttaattca aatgaaacta ttgttatctc
39301 attttaataa tgcaggtcta attcagctaa ttagtccctg gacaacagga atccttaagt
39361 aacagactat ggtgaatgcg aatttgaaag taaaagcctt gtaggcccag cccacagaag
39421 gcttcaaacc agagctctaa ttttcattgt gagtgacgtt ccctatcacc tgagaatgcg
39481 ctcactcctg gggaaccgct ctaccctctc catactgctg acatgttctg aagcagagct
39541 gccaaatcct cctatgacct cccccttgct ccttggtcac agagcttggc ccgagagatg
39601 ggaatgtcac ccaagctctg gagaaggaaa tggcagccca ctccatggaa tccatggac
39661 aaaggagcct ggcaagtcca tggggtcgaa agagttggac acgacttagt gactaaacca
39721 gcaccaccac cacctgagat ctttctagtt ggaatctagg aagacagact ttctctcagg
39781 agagacagat aggaggagtc ctcctgctga tgctgacaac cgtgatttca acctcatgga
39841 aaaaatcaga gcgaatgaaa cagacattca gagactgtat tggtatggca aagatgttcc
39901 ttgcagtccc cagggtcccc tgaactggct gtctacaag cccatcagct accccagaat
39961 cctcccaatc aatctccact ccctggtttt ctgcttaagt tgttggagt ttgctttctg
40021 ttacttgcaa ccaaaaggat attagaaaat aatagacatt aagggtcata agcaggaatg
40081 agaaagctat ggtctgtaga ctggtacagt acttgataag taaagtgtga cattttagat
40141 actaagtgct gggggttgat ccggttgat ccagggattt tgaagtgggg acgacgttgg
40201 cgaggatcag gaaacaactg cttaattaaa cattaattaa ggatataaag agtaataaa
40261 tgaggatagc tcagtgagga aactcagtgg agaaaggcgg ctgaaataag gatagctcag
40321 tgaggaaatt cagtggagat aagaggctga aataattcag ccagaaggtg agagaaagaa
40381 cgacatgggg agaccaagtt tcagtgaaca aggcccgcac tttatttttcc aaagtagttt
40441 ttataactta agttatgcat agaggataat gggggaaggg gtagagtcat gcaaggacag
40501 cagttcctga tcctaatcga agccaggctt tcaaacatat catatgcaaa agtttagatg
40561 atttacatca tcatctggcc aggaggcctg ttaacatttt aagaaactta tttttctcta
 1801 aagtgattta ttctaaagtc aggcgccagc ctccaaaaaa gcattggata aagttgcatt
 1861 cctatagggc aaaggtgtgg tgggctacaa caaaaaagaa ttaactcaag ggtccaaggt
 1921 tacaaacatt aaagctacta cttacatcaa ttatattaat caatacactg ccaaggacac
 1981 agtaggtaag gggtatggag a
```

Figure 2 (continued)

SEQUENCE LISTING

<160> NUMBER OF SEQ ID NOS: 118

<210> SEQ ID NO 1
<211> LENGTH: 4159
<212> TYPE: DNA
<213> ORGANISM: Bos taurus

<400> SEQUENCE: 1
tagcaattca gatcttgatg tgaaaatgtc agtgatctcc tcaagggtgg aaagctaact    60

```
atagctcctt gagcgccacc cttccattgc tgattcattt cctgcttccc ttttccttct      120
caaatgggtg gtgtgatatc agtaaaaggc ccagataaag tcaggacagt gcatacgcca      180
ctgctgtcta gatgttttgt gtgtgtgtgt ggtttgttgt gagccactca ggtcttaaga      240
tgttttcaac agctgtggat catttgtact caagggggag aataaaaaat aaaaaacaaa      300
cacagagact ggtgagctgg actgttagct tgagtgctaa gcatgaaagt gttcaggact      360
agaagttaga aggtgtatga tgcttaaata ttttagtgt gacagtttgg ggccagtatt      420
tttatatgta agggagctcc tgtttgtcat ttttaacgat tctgaatttg aaattcacct      480
cagttttcct ctggttcttt acgttagaaa taattcattg tgaagaatta tgaaaactga      540
cttcatttta tttaaggcgc agtgacgctg tctgtgctcc ataagtattc tgatggcact      600
gtgtcagaga gcaggggca tacccttta cgttattttt attatcactg atttttatc       660 atattattta ctaatattga ccaatattag tgaaatgctt ttagagctga gtagtatata      720 gttgccttt taacttattt ttatgaaaat gtatggtttg ataaaacttt gaaggcaccc       780
ttggattgct tcacctcctt cagaaagata acttccttca tagaagaatg ttctttcctt      840
aaaaacaaac agaaaaaatt acgtcttgga gaaggactgt tatttatt acctaaccat       900 ccacttcaga aaattctctg gtcagatatt tggcatttga aaggtaatgt ctgaccagtg      960
aaatgtttga gtgtgtttta aattactcct gatcataagt ttattttct cagagattat      1020 ccttgactgt taggtatctg tagtgcttca ttgaacgagt ttaacttata ctgttgtgat      1080
ttctagagag cttataaaat aatttgtcag ggcatgaatg tgtgggaaaa tatcagagac      1140
atctaactga gtgttttct ttatttgaga ctttaaaaaa tgtcagtagt gaagtgtcct       1200
ttaatccatt ttctttctt tgtcctctca ggtgggtctc cttacttagc aaccaaaatt       1260
aatgaagcaa aagacctgct agaagcaacc accaaacact gatggacgct caaggaccac      1320
tctgagggag aagaaggggg gccttataaa agctgtcctg cacattagtc taaaccgtgg      1380
cattcacaat ttcatatgtg caccgaccac agccatttct tccgtgtctg agctatgtga      1440
taataaaaga tgaacagtct agctttgtat tcgctttcag aggagcacat ggaaactcta      1500
gcactgatct ttccccctca ttttcttcct ctctctgata gtcatacatt tgaagacttc      1560
tactactaag ttccccgac cccagccct gcagcagtat cattatcagt aatataattg       1620
gaatttggga gcaagagtgt agaatttttt gctgcttata tttatgctcg cattgtccct      1680
tgtttcttca aaggaattta gcactctgcc tatgtgaagt gctttaaatg ttatgagacg      1740
aaaccctgac tgccaccca ggaaagtgaa ctgaagcttg atggaattta ctaaagggtg       1800
ttttgtaaag cagtggttag gaaagaacgc tgctctccca gagatcccaa ggctgtagca      1860
tgagaacttg gagagctgct aaaatgatta aaggtttaca gaatgagccc tgtgaggaaa      1920
gcctggaaat tgctgggaga agtctgaggg attcgtactt aattatatag tcttctggtg      1980
ctgtgtactt attcaattat gcattctaca aatatttatt taccacctgt agcgggtgag      2040
gtactgtagg ggtcctcagg agttccaggt gtgaaccagg cacggatcgt gacccaaagg      2100
aacttgaatt tagaggaaag ataaaccaca ggagtactat tagagaggca cagatgatag      2160
gcaaagaagt tcaaaataaa agactatttt acactgggca tcaggggc gtgtcataga       2220 atcagtagcg tagagctggg ctttaaaaac aatgagatat accatatgat gggtgagtca      2280
gaattagcag aaataggta tattagttca ttggagtgca gggttctccc aaagtaacgg       2340
atgaacacac agtctggaag ggctggccct gtaatgtgca gtgcattcaa ttatttttt       2400
```

| | |
|---|---|
| tttccccctc aacacagccc ctggttatca tcacttttct aaaagggaga aaagagagag | 2460 |
| tcagaatacc agcatatttc ttgtactgct ttacgacgct gggctcatcc caggtaaaca | 2520 |
| gaactaccac gtttcatctg tcttaaacgc tcttgtaata gtctagaggc atctttcatt | 2580 |
| ttacgacatc ctgtagttgg gagttctcag cattggtgat actgactcat tgagctgctg | 2640 |
| attcctgctt gtgggggggct ctcctgtgta tggtaggatg attagcaaca tccctgcctg | 2700 |
| cacctacgaa aggccaggag cgcccctct gttgtgacaa ccgaaaatgt atctagatgt | 2760 |
| tgccaaacgt tccttggagg gcaaaattgc cccaggtaga gagccactgc tctaaatgtt | 2820 |
| aaccgtgttc tcctttggta catgaaataa tggatggcct gacttgaaat tgattcttag | 2880 |
| gttcactgaa atacggctct cgcttaaaa tccctgtgt gtcacagttt tttgtgcttt | 2940 |
| agtatgtttt ctggcccact gctgccccgg taccttaagt gccctcctga tacccagatc | 3000 |
| tccacgtgtt caaagcctgg ggatagttga aggccaagct gaaaagtctg tctctccttt | 3060 |
| tctggtgctt ccagcaaaag taatcccatg aattgtcagc tctcagcaaa caaggattgt | 3120 |
| atctgtcttg gtcactgcta cattgacact caataaatat ttgttaaatg aacgaataca | 3180 |
| ttcccgtagc actttattct tcacatttgg taacttgtga aacaactctt tgtgtgacat | 3240 |
| gacttatttc ttctacaaaa gtacaagaac ctttagagca agaatcttgt catttgtctt | 3300 |
| tgtaacctcc ttaagagtgg agcacttggg actttgtaga catcataaag ttgtaagtac | 3360 |
| taaaaaaat gttttttgaa tactatgctt caaaaaatgt aaccactagt tttgaaagtt | 3420 |
| atgttatgca atattggggt accctcagaa catacctgtt agttgacatc attttctagt | 3480 |
| ccacactgtg ttcatgaaaa tttaagtcct cagcactagc ttgaaatttc cttcattcta | 3540 |
| ttctcattta tctgttgagt gtgtgcccaa aaatcagaca cctggtttta agtactatcc | 3600 |
| tcctatcaca taatctgggg caattaatct gcaaggcttt aattgcctca tctataaaat | 3660 |
| agagaaaata ataaccctat ctaaaaggt ccatctagtc aaggctatgg ttttccagt | 3720 |
| ggtcatgtat ggatgtgaga gttggactgt gaagaaggct gagcgccgaa gaattgatgc | 3780 |
| ttttgaactg tggtgttgga aagactctt gagagtccct tggactgcaa ggacatccaa | 3840 |
| ccagtccatc ctaaaggaga tcagtcctgg gtgttcattg gagggactga tgctgaagct | 3900 |
| gaaactccaa tactttggcc acctcatgcg aagagctgac tcattggaaa agaccctgat | 3960 |
| gctgggaggg gttgggggca ggaggagaag gggacgacag aggatgagat ggctggatgg | 4020 |
| catcaccaac tcgatggatg tgagtttggg taagctccgg gagttggtgc tggacaggga | 4080 |
| ggcctggcat gctgcgattc atggggttgc aaagagtcgg acacgactga gtgactgaac | 4140 |
| tgaactgaaa aaggttgtt | 4159 |

```
<210> SEQ ID NO 2
<211> LENGTH: 6741
<212> TYPE: DNA
<213> ORGANISM: Bos taurus

<400> SEQUENCE: 2
```

| | |
|---|---|
| ttgctcagtt gtgcccgact ctttgcaacc ccatggactg tagcctacta ggttccttgc | 60 |
| tccatgggat tctccaggca agagtaccag agtgggttgc catttccttc tccagaggat | 120 |
| cttcctgacc cagggatcga acccaggtct cccgcattcc aggcagacac tttaacctct | 180 |
| gagccactag ggatgggaag agggagacag ttattggtca cccttgattt gacaagcgtt | 240 |
| actgaggatg ctttaaacac ctgacgaaat tcagatgacc ttgtagcgta aagttaattg | 300 |
| gtggcttttg gggcttccca ggtggcacag tggtaaagaa tctgcctgcc catgcaagag | 360 |

```
atgcaagaga cttgggttcg atccctgggt ggggaagatc ctctgaagaa gggaatggcc      420
acccactcca gtattcttgc ctggagaatt ccatggacag aggagcctgg tgggctacag      480
gccatagggt tgcaaagagt cgggcacaac tgagcaacta atattacttt tactattgta      540
tatcaaattc agctttttg ttgttttgtc ctttccctta tggaccctgc tccctggctg       600
actttgtccg ctgtttgctt ctggaactac atgccgtgtc tctgttccct ctctggcctc      660
tgccatttct ttccctgcgg ctctgtgttt cccatcaccg gatcaattcc tgaaacccat      720
cttcttgcag agtcctcctc caggggggcc ttgccctgat ggcctcttgt cctcatcgct      780
tccatcagca attatttgct gagtgccaaa tgcctgtgag cgctaacca ctaattttca       840
gttgattatg tttgtatact cactttgtat tgtctgtttt tctacttgaa tgttacatat      900
tatttgtcca ttgtttgttt cccagtcctt tagtctaacc tttgagaaag ggtcacgata      960
atttcagata tgcttactgc aagaggtgtt ctgttatcca ggcagctgaa atgcagtgga     1020
cagagggtgg ggctgacctc cctactgaca tagagctctg ctttttcttt gcagggatga     1080
agtcaataaa gcatatcgga agcttgctgt gctgcttcac cctgacaaat gtgtagcacc     1140
tggtagtgaa gatgccttca aagccgttgt gaatgcccga acagccctcc tgaaaaacat     1200
caagtagaaa ataggaaaaa agacaggtg taggcctcga gtccaaacag actttctctg      1260
gaagtaaaat agccaacatg gttttttcct ccacaaaatt cttacagccc ttttcactca     1320
cgtgctgtca tttgtgaatc agtaatttgg ctgcctgttt ccatgtcaca gacattttgc     1380
agagagacaa aatgaagaga accgagtgcc acttatacac tgtcgttcat tttctatttc     1440
tgaatgatga tagattttt ttttttttctc atgagttggt aagctgtcgg tatagcatca     1500
cttgggcact ttgctcagga aagtccacaa agtttctgga agaaggatag gaggatcctt     1560
ttgcttttc tttattaaaa aaacattcat catcagagga aaaaaaaaca aaaatggaag     1620
cagacatagt agaacccctg aaagtgtggt gactttacaa gcaagttgcc cctttacaat     1680
gagtttctaa ggtgatattt taagcatcag tctgcttaat taatgaatga actcttggca     1740
gcccttcgga agtgaaacaa ggtgatgcta tcctgagctg agtggccctt ttttgacgtt     1800
cggtctgtgc cccttctcca tcaccggggg agagaccagc cagtcctgag agtagaggtg     1860
gcggtagccg caggtctgg tagactggct gctgctagac ctgcccctgg gtctgaggcc      1920
tttccctggc cgtgggagtg ctggtagctg taggggcatc ttcacctagg agtctggagt     1980
cagatcccaa gacacaaatg cctgcaggtc aaactggatt gtgtacacat tcccagaggg     2040
cctgacccgc ctggttcggg cgtgtctgat gccctaggag agcccccata ggaggcttat     2100
gcctttcctt gttgcagcat catttgccaa gacaggtggg aaatgcaggg ttgcgtctca     2160
acaggggggcc tcccttcgct tcctcgtcag tgtgagctcc ccttccctct tctgttcctg     2220
ccttgtctct caaggcaccg catctgccac cacgtctctc ttctcgaatc cccaccttcc     2280
ggctattgcc tcctctgtcc tgtgcagcct tgctgggc ctggtagacc agagacaagt       2340
atagatcctt ggggtggtgg atggagagat cttaaggcct gtgtgggaag aatttgttac     2400
ttttgtttag gttccaaatt tctgatcagt aatacttta agctgcagat tatgaaaatt     2460
aatttcacat agagaaatcc attctcttgc tatcgtctgt ctctcagtat ccaagagatg     2520
gatgaagatc aagtgtcagg accggccttc cttccagagc tcacagaata gagtcaccac     2580
gtggcgtgtt acaccatcac tctcacgtta ctcagattgt tagctgtgac caagctgcac     2640
taattggggc tttaaagtat atgaagcttt gccatcagtg aattttaagc agctatccca     2700
```

```
tattgattgc caagtagcat tcgccttacc ctacctgaga agaaaaacca ctttcattta    2760
attcaaaccc actgcagctt actgaaccct tcccttctcc agagcagctt cgctttgtgt    2820
ggctactctt gggcagcact gagctggttg tcaggaaacc agagcattgt tttctagtaa    2880
gagttttcat tttgatatta aaaatgcttt tttttcttag taaaattgag atatgagata    2940
tgattttttg tgggattttc ctcttgcctt ttaattttaa ctagcttctg ggcctgtaaa    3000
actcaggcca aagttcttca gggttttaat tttgctgttg gccttcatca tggccaaagt    3060
aacaaacata gatctgttct tgtggcagaa cttaagagtc acatgagtga ggaactgtgc    3120
atggtggtgt cagcccacat tgacatgaca gctcacttgt gtatgtggcc ctgtgtaaaa    3180
actggtgcca gttttcatca ctgtcattaa acactagatg ggtcacctca ttcagctaca    3240
ttgtgcagat gagcagttat agcagataga gttctctagt tcttccattc acatccttat    3300
gtaatgagtg acttgttgac atttagcctg gtcttgattc ttaggtcttg ctcagttccc    3360
agcaccttga ttactaatgt taaggatggc catgtactac ttcatttatg gaaaagaaag    3420
aaaagaaaga taaaggttca gggtcctaga attttttctga tttccataat cctgagtaga    3480
atgtcaagaa gtaatgaaat gaagcctgat ctgcaatgaa agtaacttc atataaaatt     3540
ttacagacct ctgtgcatta atttaaattc ttggtacaaa tgtatatttt ttagttcaac    3600
cttattaaaa ttcttcagcc agttaggatt gcacaataca tcagtgagag taacaactag    3660
cagataatt tcaatggcta aaaaaaattt tatacagaat cttgtttttt caaaaaagaa     3720
caagaagttt gaacagctgt tattcaagaa aagccatttc ttgggcatct gagtcaccaa    3780
gaatgaacac tttaaaaact tgttagaaat ccctggaggt ttttgaaatt aatcgccaac    3840
ctacctaaga acttaaaaat ataccatcct tttgttcctc ccttcctctt tcatggctcc    3900
ttttgaatca atattctcaa ctgtcaacgt gtctcttact tcagcaatgt cgtttatttc    3960
tttgcatgaa tgtgtgcttg gtaaagtctg gacttggaga tgttgtgctg cttcccaaga    4020
taaattgctc tgattctgta gattgcactc tgtgctttaa ggctcacatt tacctcagga    4080
aactcacttt agtatgtttt gttttgtttt gggttttttt gcattgaatt ctcaaatggt    4140
aattatttct ttatactggt aaactagtac ctaatttact gttcactaag tgagccatag    4200
ataaggcagc taaatttctg aaagaaagaa aaaataggca gcccttgatt gctgtgaatc    4260
agtaataagg tccctatttc tcaaagagca atgacagaat ctcaagggga aggaggtatt    4320
tcggtctcat gttagaaagg gggggggttg tgcacattgc ctttgacagg gtgtcagtat    4380
ctgtccccta agcaatttca gtgggcccta gaatgtcact cccttctcta ctacactctg    4440
tctagctcac tctgagtctg actacatttt tgtgaaactt ttgcagagaa attaagccgc    4500
aaaatggagc taacctcctt ccattgcaag ttttgcaaag ggaagagggg ttcatatttc    4560
tcatgatagg tacctagcac aattgtaaga gacagttact aatgtttata tgttggtgtt    4620
tccattaagc atttctagag gagacgaaag cttaaacttg tggtgtggat gagttagatc    4680
gtgtctgaca agcagtgcaa tatgaagctg tgcaataaag gctgtgttgt gaaatgaagc    4740
actggaaagc tggacagttc gggttagctt cctgcagcaa ttgcccgcag gatggtctgc    4800
ccttggccca ggaatgcaaa gaaaccctt gctcttacga ggtaatttat gtatttgctt      4860
tctgttgaaa taatggaaaa tgttaaagct aacagctgtc tatgtcttgt atagagagtg    4920
tcatatgtat ttaagttgtg tattttata aagtaaagcc aaatgccaaa tactggtctg     4980
tgggctgcac tcatttgttg agacactggt cttttgaagca gaagctggcc gttaccgact   5040
gagatcatag ataagacatc ttgctttagt tgccagtggg taaaatgaag gaaatggtat    5100
```

```
tcagtggtcc ctcaggctgt tctaacctta attaagttgt gatgaaagtc tctgctctct    5160
taaagaaaga tactaatatt atgtttgcct ttttaattca aatgaaacta ttgttatctc    5220 atttttaataa tgcaggtcta attcagctaa ttagtccctg gacaacagga atccttaagt   5280
aacagactat ggtgaatgcg aatttgaaag taaaagcctt gtaggcccag cccacagaag    5340
gcttcaaacc agagctctaa ttttcattgt gagtgacgtt ccctatcacc tgagaatgcg    5400
ctcactcctg gggaaccgct ctaccctctc catactgctg acatgttctg aagcagagct    5460
gccaaatcct cctatgacct ccccccttgct ccttggtcac agagcttggc ccgagagatg   5520
ggaatgtcac ccaagctctg gagaaggaaa tggcagccca ctccatggaa tcccatggac    5580
aaaggagcct ggcaagtcca tggggtcgaa agagttggac acgacttagt gactaaacca    5640
gcaccaccac cacctgagat ctttctagtt ggaatctagg aagacagact ttctctcagg    5700
agagacagat aggaggagtc ctcctgctga tgctgacaac cgtgatttca acctcatgga    5760
aaaaatcaga gcgaatgaaa cagacattca gagactgtat tggtatggca agatgttcc     5820 ttgcagtccc cagggtcccc tgaactggct gctctacaag cccatcagct accccagaat    5880
cctcccaatc aatctccact ccctggtttt ctgcttaagt tgttggagt ttgctttctg     5940 ttacttgcaa ccaaaaggat attagaaaat aatagacatt aagggtcata agcaggaatg    6000
agaaagctat ggtctgtaga ctggtacagt acttgataag taaagtgtga cattttagat    6060
actaagtgct ggggtccagc cctggttgat ccagggaatt tgaagtgggg acgacgttgg    6120
cgaggatcag gaaacaactg cttaattaaa cattaattaa ggatataaag agtaatagaa    6180
tgaggatagc tcagtgagga aactcagtgg agaaaggcgg ctgaaataag gatagctcag    6240
tgaggaaatt cagtggagat aagaggctga ataattcag ccagaaggtg agagaaagaa     6300
cgacatgggg agaccaagtt tcagtgaaca aggcccgcac tttatttttcc aaagtagttt    6360 ttataccctta agttatgcat agaggataat gggggaaggg gtagagtcat gcaaggacag   6420
cagttcctga tcctaatcga agccaggctt tcaaacatat catatgcaaa gtttagatg    6480 atttacatca tcatctggcc aggaggcctg ttaacatttt aagaaactta tttttctcta    6540
aaggtgatta ttctaaagtc aggcgccagc ctccaaaaaa gcattggata aagttgcatt    6600
cctatagggc aaaggtgtgg tgggctacaa caaaaaagaa ttaactcaag ggtccaaggt    6660
tacaaacatt aaagctacta cttacatcaa ttatattaat caatcactg ccaaggacac     6720 agtaggtaag gggtatggag a                                              6741
```

<210> SEQ ID NO 3
<211> LENGTH: 18
<212> TYPE: DNA
<213> ORGANISM: Artificial Sequence
<220> FEATURE:
<223> OTHER INFORMATION: primer GAPDH-F

<400> SEQUENCE: 3
tgcccagaat atcatccc                                                    18

<210> SEQ ID NO 4
<211> LENGTH: 18
<212> TYPE: DNA
<213> ORGANISM: Artificial Sequence
<220> FEATURE:
<223> OTHER INFORMATION: primer GAPDH-R

<400> SEQUENCE: 4
aggtcagatc cacaacag                                                    18

<210> SEQ ID NO 5
<211> LENGTH: 20
<212> TYPE: DNA
<213> ORGANISM: Artificial Sequence
<220> FEATURE:
<223> OTHER INFORMATION: primer DNAJC5-F

<400> SEQUENCE: 5
ctacgacaag tacggctcac                                                  20

<210> SEQ ID NO 6
<211> LENGTH: 18
<212> TYPE: DNA
<213> ORGANISM: Artificial Sequence
<220> FEATURE:
<223> OTHER INFORMATION: primer DNAJC5-R

<400> SEQUENCE: 6
ggcagcagca acagtagc                                                    18

<210> SEQ ID NO 7
<211> LENGTH: 19
<212> TYPE: DNA
<213> ORGANISM: Artificial Sequence
<220> FEATURE:
<223> OTHER INFORMATION: Primer DNAJC15-F

<400> SEQUENCE: 7
aggtcgctac gcatttcag                                                   19

<210> SEQ ID NO 8
<211> LENGTH: 20
<212> TYPE: DNA
<213> ORGANISM: Artificial Sequence
<220> FEATURE:
<223> OTHER INFORMATION: primer DNAJC15-R

<400> SEQUENCE: 8
gacttgcttc tcgcctactc                                                  20

<210> SEQ ID NO 9
<211> LENGTH: 19
<212> TYPE: DNA
<213> ORGANISM: Artificial Sequence
<220> FEATURE:
<223> OTHER INFORMATION: primer DNAJC19-F

<400> SEQUENCE: 9
ggactgacca ttgctgctg                                                   19

<210> SEQ ID NO 10
<211> LENGTH: 21
<212> TYPE: DNA
<213> ORGANISM: Artificial Sequence
<220> FEATURE:
<223> OTHER INFORMATION: primer DNAJC19-R

<400> SEQUENCE: 10
caaacccacc tctgtaatag c                                                21

<210> SEQ ID NO 11
<211> LENGTH: 22
<212> TYPE: DNA
<213> ORGANISM: Artificial Sequence

```
<220> FEATURE:
<223> OTHER INFORMATION: primer DNAJC24-F

<400> SEQUENCE: 11
gaaatatggg accagtagat gc                                              22

<210> SEQ ID NO 12
<211> LENGTH: 22
<212> TYPE: DNA
<213> ORGANISM: Artificial Sequence
<220> FEATURE:
<223> OTHER INFORMATION: primer DNAJC24-R

<400> SEQUENCE: 12
tgtaacttct tctgcttcat cc                                              22

<210> SEQ ID NO 13
<211> LENGTH: 19
<212> TYPE: DNA
<213> ORGANISM: Artificial Sequence
<220> FEATURE:
<223> OTHER INFORMATION: primer DNAJC27-F

<400> SEQUENCE: 13
aacaagcgga caccattcg                                                  19

<210> SEQ ID NO 14
<211> LENGTH: 18
<212> TYPE: DNA
<213> ORGANISM: Artificial Sequence
<220> FEATURE:
<223> OTHER INFORMATION: primer DNAJC27-R

<400> SEQUENCE: 14
tgaagcagca cagcaagc                                                   18

<210> SEQ ID NO 15
<211> LENGTH: 22
<212> TYPE: DNA
<213> ORGANISM: Artificial Sequence
<220> FEATURE:
<223> OTHER INFORMATION: primer HSPA5-F

<400> SEQUENCE: 15
caaccaactg ttaccatcaa gg                                              22

<210> SEQ ID NO 16
<211> LENGTH: 21
<212> TYPE: DNA
<213> ORGANISM: Artificial Sequence
<220> FEATURE:
<223> OTHER INFORMATION: primer HSPA5-R

<400> SEQUENCE: 16
aaaggtgact tcaatctgtg g                                               21

<210> SEQ ID NO 17
<211> LENGTH: 19
<212> TYPE: DNA
<213> ORGANISM: Artificial Sequence
<220> FEATURE:
<223> OTHER INFORMATION: primer HSPA9-F

<400> SEQUENCE: 17
gaccaactgc ctgctgatg                                                  19
```

```
<210> SEQ ID NO 18
<211> LENGTH: 18
<212> TYPE: DNA
<213> ORGANISM: Artificial Sequence
<220> FEATURE:
<223> OTHER INFORMATION: primer HSPA9-R

<400> SEQUENCE: 18
gatgccgcct gccttatg                                                  18

<210> SEQ ID NO 19
<211> LENGTH: 18
<212> TYPE: DNA
<213> ORGANISM: Artificial Sequence
<220> FEATURE:
<223> OTHER INFORMATION: primer HSPA8-F

<400> SEQUENCE: 19
cgcagaagcc taccttgg                                                  18

<210> SEQ ID NO 20
<211> LENGTH: 21
<212> TYPE: DNA
<213> ORGANISM: Artificial Sequence
<220> FEATURE:
<223> OTHER INFORMATION: primer HSPA8-R

<400> SEQUENCE: 20
gttgagacca gcaatagttc c                                              21

<210> SEQ ID NO 21
<211> LENGTH: 21
<212> TYPE: DNA
<213> ORGANISM: Artificial Sequence
<220> FEATURE:
<223> OTHER INFORMATION: primer HSPA14-F

<400> SEQUENCE: 21
aaccttagca cagtacctag c                                              21

<210> SEQ ID NO 22
<211> LENGTH: 19
<212> TYPE: DNA
<213> ORGANISM: Artificial Sequence
<220> FEATURE:
<223> OTHER INFORMATION: primer HSPA14-R

<400> SEQUENCE: 22
tgtcagcacc gttcatcag                                                 19

<210> SEQ ID NO 23
<211> LENGTH: 20
<212> TYPE: DNA
<213> ORGANISM: Artificial Sequence
<220> FEATURE:
<223> OTHER INFORMATION: primer HSBP1-F

<400> SEQUENCE: 23
catgtccgac cagatcattg                                                20

<210> SEQ ID NO 24
<211> LENGTH: 19
<212> TYPE: DNA
<213> ORGANISM: Artificial Sequence
<220> FEATURE:
<223> OTHER INFORMATION: primer HSBP1-R
```

```
<400> SEQUENCE: 24
ttcactgtcc agctcttcc                                              19

<210> SEQ ID NO 25
<211> LENGTH: 20
<212> TYPE: DNA
<213> ORGANISM: Artificial Sequence
<220> FEATURE:
<223> OTHER INFORMATION: primer HSBP1-F

<400> SEQUENCE: 25
catgtccgac cagatcattg                                             20

<210> SEQ ID NO 26
<211> LENGTH: 19
<212> TYPE: DNA
<213> ORGANISM: Artificial Sequence
<220> FEATURE:
<223> OTHER INFORMATION: primer HSBP1-R

<400> SEQUENCE: 26
ttcactgtcc agctcttcc                                              19

<210> SEQ ID NO 27
<211> LENGTH: 22
<212> TYPE: DNA
<213> ORGANISM: Artificial Sequence
<220> FEATURE:
<223> OTHER INFORMATION: primer DNAJB1-F

<400> SEQUENCE: 27
gaggagaagt tcaaggagat cg                                          22

<210> SEQ ID NO 28
<211> LENGTH: 18
<212> TYPE: DNA
<213> ORGANISM: Artificial Sequence
<220> FEATURE:
<223> OTHER INFORMATION: primer DNAJB1-R

<400> SEQUENCE: 28
ttagtaccgc cgctgctc                                               18

<210> SEQ ID NO 29
<211> LENGTH: 21
<212> TYPE: DNA
<213> ORGANISM: Artificial Sequence
<220> FEATURE:
<223> OTHER INFORMATION: primer DNAJB12-F

<400> SEQUENCE: 29
gcaaactagc cctcaaattc c                                           21

<210> SEQ ID NO 30
<211> LENGTH: 20
<212> TYPE: DNA
<213> ORGANISM: Artificial Sequence
<220> FEATURE:
<223> OTHER INFORMATION: primer DNAJB12-R

<400> SEQUENCE: 30
ccttgtcatc accgaactgg                                             20

<210> SEQ ID NO 31
```

<210> SEQ ID NO 31
<211> LENGTH: 22
<212> TYPE: DNA
<213> ORGANISM: Artificial Sequence
<220> FEATURE:
<223> OTHER INFORMATION: primer DNAJC14-F

<400> SEQUENCE: 31
gtgaatgagt tctgtccaa gc          22

<210> SEQ ID NO 32
<211> LENGTH: 22
<212> TYPE: DNA
<213> ORGANISM: Artificial Sequence
<220> FEATURE:
<223> OTHER INFORMATION: primer DNAJC14-R

<400> SEQUENCE: 32
gtatctggca ctcttaggtt cc          22

<210> SEQ ID NO 33
<211> LENGTH: 20
<212> TYPE: DNA
<213> ORGANISM: Artificial Sequence
<220> FEATURE:
<223> OTHER INFORMATION: primer HSPA2-F

<400> SEQUENCE: 33
acgctgtgga gtcctatacc          20

<210> SEQ ID NO 34
<211> LENGTH: 18
<212> TYPE: DNA
<213> ORGANISM: Artificial Sequence
<220> FEATURE:
<223> OTHER INFORMATION: primer HSPA2-R

<400> SEQUENCE: 34
ttccgccatc tggttccg          18

<210> SEQ ID NO 35
<211> LENGTH: 21
<212> TYPE: DNA
<213> ORGANISM: Artificial Sequence
<220> FEATURE:
<223> OTHER INFORMATION: primer HSPA4-F

<400> SEQUENCE: 35
tcctgcctta gaagagaaac c          21

<210> SEQ ID NO 36
<211> LENGTH: 20
<212> TYPE: DNA
<213> ORGANISM: Artificial Sequence
<220> FEATURE:
<223> OTHER INFORMATION: primer HSPA4-R

<400> SEQUENCE: 36
cccagtgttg tgtcaaatgc          20

<210> SEQ ID NO 37
<211> LENGTH: 22
<212> TYPE: DNA
<213> ORGANISM: Artificial Sequence
<220> FEATURE:
<223> OTHER INFORMATION: primer HSPH1-F

<400> SEQUENCE: 37

```
atgttgagtt gcctattgaa gc                                          22
```

<210> SEQ ID NO 38
<211> LENGTH: 19
<212> TYPE: DNA
<213> ORGANISM: Artificial Sequence
<220> FEATURE:
<223> OTHER INFORMATION: primer HSPH1-R

<400> SEQUENCE: 38

```
cctccaccgc attcttagc                                              19
```

<210> SEQ ID NO 39
<211> LENGTH: 18
<212> TYPE: DNA
<213> ORGANISM: Artificial Sequence
<220> FEATURE:
<223> OTHER INFORMATION: primer DNAJC5-667-F

<400> SEQUENCE: 39

```
aggagacgga gttctatg                                               18
```

<210> SEQ ID NO 40
<211> LENGTH: 17
<212> TYPE: DNA
<213> ORGANISM: Artificial Sequence
<220> FEATURE:
<223> OTHER INFORMATION: primer DNAJC5-667-R

<400> SEQUENCE: 40

```
cacgttcaca cctcaac                                                17
```

<210> SEQ ID NO 41
<211> LENGTH: 18
<212> TYPE: DNA
<213> ORGANISM: Artificial Sequence
<220> FEATURE:
<223> OTHER INFORMATION: primer DNAJC5-725-F

<400> SEQUENCE: 41

```
ggccctgttc atcttctg                                               18
```

<210> SEQ ID NO 42
<211> LENGTH: 17
<212> TYPE: DNA
<213> ORGANISM: Artificial Sequence
<220> FEATURE:
<223> OTHER INFORMATION: primer DNAJC5-725-R

<400> SEQUENCE: 42

```
ggcacagacc ctctcat                                                17
```

<210> SEQ ID NO 43
<211> LENGTH: 20
<212> TYPE: DNA
<213> ORGANISM: Artificial Sequence
<220> FEATURE:
<223> OTHER INFORMATION: primer DNAJC5-1049-F

<400> SEQUENCE: 43

```
gggttcaact aaatccagga                                             20
```

<210> SEQ ID NO 44
<211> LENGTH: 18
<212> TYPE: DNA

<213> ORGANISM: Artificial Sequence
<220> FEATURE:
<223> OTHER INFORMATION: primer DNAJC5-1049-R

<400> SEQUENCE: 44
acgccatctc tgtgacta                                                18

<210> SEQ ID NO 45
<211> LENGTH: 24
<212> TYPE: DNA
<213> ORGANISM: Artificial Sequence
<220> FEATURE:
<223> OTHER INFORMATION: primer DNAJC19-475-F

<400> SEQUENCE: 45
ggatctcctt atatagcagc caaa                                         24

<210> SEQ ID NO 46
<211> LENGTH: 18
<212> TYPE: DNA
<213> ORGANISM: Artificial Sequence
<220> FEATURE:
<223> OTHER INFORMATION: primer DNAJC19-475-R

<400> SEQUENCE: 46
agccttccct cccagtga                                                18

<210> SEQ ID NO 47
<211> LENGTH: 20
<212> TYPE: DNA
<213> ORGANISM: Artificial Sequence
<220> FEATURE:
<223> OTHER INFORMATION: primer DNAJC19-536-F

<400> SEQUENCE: 47
atgctcatcg gcgaattatg                                              20

<210> SEQ ID NO 48
<211> LENGTH: 20
<212> TYPE: DNA
<213> ORGANISM: Artificial Sequence
<220> FEATURE:
<223> OTHER INFORMATION: primer DNAJC19-536-R

<400> SEQUENCE: 48
agctggaacg cataagagaa                                              20

<210> SEQ ID NO 49
<211> LENGTH: 19
<212> TYPE: DNA
<213> ORGANISM: Artificial Sequence
<220> FEATURE:
<223> OTHER INFORMATION: primer DNAJC24-628-F

<400> SEQUENCE: 49
ctcattttaa tggaagatg                                               19

<210> SEQ ID NO 50
<211> LENGTH: 18
<212> TYPE: DNA
<213> ORGANISM: Artificial Sequence
<220> FEATURE:
<223> OTHER INFORMATION: primer DNAJC24-628-R

<400> SEQUENCE: 50
gtatcacaag aaatcagt                                                18

<210> SEQ ID NO 51
<211> LENGTH: 18
<212> TYPE: DNA
<213> ORGANISM: Artificial Sequence
<220> FEATURE:
<223> OTHER INFORMATION: primer DNAJC24-2172-F

<400> SEQUENCE: 51
catccagata aacagagt                                                 18

<210> SEQ ID NO 52
<211> LENGTH: 19
<212> TYPE: DNA
<213> ORGANISM: Artificial Sequence
<220> FEATURE:
<223> OTHER INFORMATION: primer DNAJC24-2172-R

<400> SEQUENCE: 52
ggtcccatat ttcttagat                                                19

<210> SEQ ID NO 53
<211> LENGTH: 20
<212> TYPE: DNA
<213> ORGANISM: Artificial Sequence
<220> FEATURE:
<223> OTHER INFORMATION: primer DNAJC24-1893-F

<400> SEQUENCE: 53
caaaagaaag tatctcattc                                               20

<210> SEQ ID NO 54
<211> LENGTH: 19
<212> TYPE: DNA
<213> ORGANISM: Artificial Sequence
<220> FEATURE:
<223> OTHER INFORMATION: primer DNAJC24-1893-R

<400> SEQUENCE: 54
taacttcttc tgcttcatc                                                19

<210> SEQ ID NO 55
<211> LENGTH: 20
<212> TYPE: DNA
<213> ORGANISM: Artificial Sequence
<220> FEATURE:
<223> OTHER INFORMATION: primer DNAJB12-1220-F

<400> SEQUENCE: 55
accgactgtc agagactatg                                               20

<210> SEQ ID NO 56
<211> LENGTH: 18
<212> TYPE: DNA
<213> ORGANISM: Artificial Sequence
<220> FEATURE:
<223> OTHER INFORMATION: primer DNAJB12-1220-R

<400> SEQUENCE: 56
cggcctccaa ttccattt                                                 18

<210> SEQ ID NO 57
<211> LENGTH: 19
<212> TYPE: DNA
<213> ORGANISM: Artificial Sequence
<220> FEATURE:

```
<223> OTHER INFORMATION: primer DNAJC15-1-F

<400> SEQUENCE: 57
ccggaggtct gcaaatggg                                                    19

<210> SEQ ID NO 58
<211> LENGTH: 22
<212> TYPE: DNA
<213> ORGANISM: Artificial Sequence
<220> FEATURE:
<223> OTHER INFORMATION: primer DNAJC15-1-R

<400> SEQUENCE: 58
aactgctcgc ctggtgctgg tc                                                22

<210> SEQ ID NO 59
<211> LENGTH: 20
<212> TYPE: DNA
<213> ORGANISM: Artificial Sequence
<220> FEATURE:
<223> OTHER INFORMATION: primer DNAJC15-2-F

<400> SEQUENCE: 59
tcactgaaaa tcagccaata                                                   20

<210> SEQ ID NO 60
<211> LENGTH: 18
<212> TYPE: DNA
<213> ORGANISM: Artificial Sequence
<220> FEATURE:
<223> OTHER INFORMATION: primer DNAJC15-2-R

<400> SEQUENCE: 60
cgtacagaag agccccat                                                     18

<210> SEQ ID NO 61
<211> LENGTH: 22
<212> TYPE: DNA
<213> ORGANISM: Artificial Sequence
<220> FEATURE:
<223> OTHER INFORMATION: primer DNAJC15-3-F

<400> SEQUENCE: 61
aattgcttta ttactttagc gg                                                22

<210> SEQ ID NO 62
<211> LENGTH: 20
<212> TYPE: DNA
<213> ORGANISM: Artificial Sequence
<220> FEATURE:
<223> OTHER INFORMATION: primer DNAJC15-3-R

<400> SEQUENCE: 62
agggaccatg tctgttttgt                                                   20

<210> SEQ ID NO 63
<211> LENGTH: 20
<212> TYPE: DNA
<213> ORGANISM: Artificial Sequence
<220> FEATURE:
<223> OTHER INFORMATION: primer DNAJC15-4-F

<400> SEQUENCE: 63
aaagtccctg tagagcttag                                                   20
```

```
<210> SEQ ID NO 64
<211> LENGTH: 20
<212> TYPE: DNA
<213> ORGANISM: Artificial Sequence
<220> FEATURE:
<223> OTHER INFORMATION: primer DNAJC15-4-R

<400> SEQUENCE: 64
ataaaggcac atcacaacta                                                   20

<210> SEQ ID NO 65
<211> LENGTH: 20
<212> TYPE: DNA
<213> ORGANISM: Artificial Sequence
<220> FEATURE:
<223> OTHER INFORMATION: primer DNAJC15-5-F

<400> SEQUENCE: 65
tcctcctgtc ctagttcttg                                                   20

<210> SEQ ID NO 66
<211> LENGTH: 20
<212> TYPE: DNA
<213> ORGANISM: Artificial Sequence
<220> FEATURE:
<223> OTHER INFORMATION: primer DNAJC15-5-R

<400> SEQUENCE: 66
ttcattatgc ccaaatcagt                                                   20

<210> SEQ ID NO 67
<211> LENGTH: 20
<212> TYPE: DNA
<213> ORGANISM: Artificial Sequence
<220> FEATURE:
<223> OTHER INFORMATION: primer DNAJC15-6-F

<400> SEQUENCE: 67
ccatccactt cagaaaattc                                                   20

<210> SEQ ID NO 68
<211> LENGTH: 22
<212> TYPE: DNA
<213> ORGANISM: Artificial Sequence
<220> FEATURE:
<223> OTHER INFORMATION: primer DNAJC15-6-R

<400> SEQUENCE: 68
ggggaaagat cagtgctaga gt                                                22

<210> SEQ ID NO 69
<211> LENGTH: 20
<212> TYPE: DNA
<213> ORGANISM: Artificial Sequence
<220> FEATURE:
<223> OTHER INFORMATION: primer DNAJC19-1-F

<400> SEQUENCE: 69
ttttccgacc tagtttacgg                                                   20

<210> SEQ ID NO 70
<211> LENGTH: 21
<212> TYPE: DNA
<213> ORGANISM: Artificial Sequence
<220> FEATURE:
<223> OTHER INFORMATION: primer DNAJC19-1-R
```

```
<400> SEQUENCE: 70
acttctactt caccacaggg a                                             21

<210> SEQ ID NO 71
<211> LENGTH: 20
<212> TYPE: DNA
<213> ORGANISM: Artificial Sequence
<220> FEATURE:
<223> OTHER INFORMATION: primer DNAJC19-2-F

<400> SEQUENCE: 71
agccgcatac ctttacaatg                                               20

<210> SEQ ID NO 72
<211> LENGTH: 20
<212> TYPE: DNA
<213> ORGANISM: Artificial Sequence
<220> FEATURE:
<223> OTHER INFORMATION: primer DNAJC19-2-R

<400> SEQUENCE: 72
atgggtcact tcagattcct                                               20

<210> SEQ ID NO 73
<211> LENGTH: 20
<212> TYPE: DNA
<213> ORGANISM: Artificial Sequence
<220> FEATURE:
<223> OTHER INFORMATION: primer DNAJC19-3-F

<400> SEQUENCE: 73
tcccagaaga actgggtttg                                               20

<210> SEQ ID NO 74
<211> LENGTH: 20
<212> TYPE: DNA
<213> ORGANISM: Artificial Sequence
<220> FEATURE:
<223> OTHER INFORMATION: primer DNAJC19-3-R

<400> SEQUENCE: 74
agatggaagt ccctggcagt                                               20

<210> SEQ ID NO 75
<211> LENGTH: 20
<212> TYPE: DNA
<213> ORGANISM: Artificial Sequence
<220> FEATURE:
<223> OTHER INFORMATION: primer DNAJC19-4-F

<400> SEQUENCE: 75
tttaactcac tggaggtagg                                               20

<210> SEQ ID NO 76
<211> LENGTH: 20
<212> TYPE: DNA
<213> ORGANISM: Artificial Sequence
<220> FEATURE:
<223> OTHER INFORMATION: primer DNAJC19-4-R

<400> SEQUENCE: 76
accaaaacag caagtagacc                                               20

<210> SEQ ID NO 77
<211> LENGTH: 20
```

```
<212> TYPE: DNA
<213> ORGANISM: Artificial Sequence
<220> FEATURE:
<223> OTHER INFORMATION: primer DNAJC19-5-F

<400> SEQUENCE: 77
agggattgtt gataactgga                                            20

<210> SEQ ID NO 78
<211> LENGTH: 20
<212> TYPE: DNA
<213> ORGANISM: Artificial Sequence
<220> FEATURE:
<223> OTHER INFORMATION: primer DNAJC19-5-R

<400> SEQUENCE: 78
tttataccaa cgctttgact                                            20

<210> SEQ ID NO 79
<211> LENGTH: 18
<212> TYPE: DNA
<213> ORGANISM: Artificial Sequence
<220> FEATURE:
<223> OTHER INFORMATION: primer DNAJC24-1-F

<400> SEQUENCE: 79
gctcggctgg aaacttga                                              18

<210> SEQ ID NO 80
<211> LENGTH: 18
<212> TYPE: DNA
<213> ORGANISM: Artificial Sequence
<220> FEATURE:
<223> OTHER INFORMATION: primer DNAJC24-1-R

<400> SEQUENCE: 80
cggtggatgg ccctctaa                                              18

<210> SEQ ID NO 81
<211> LENGTH: 20
<212> TYPE: DNA
<213> ORGANISM: Artificial Sequence
<220> FEATURE:
<223> OTHER INFORMATION: primer DNAJC24-2-F

<400> SEQUENCE: 81
ccatttcctt ctccactagt                                            20

<210> SEQ ID NO 82
<211> LENGTH: 20
<212> TYPE: DNA
<213> ORGANISM: Artificial Sequence
<220> FEATURE:
<223> OTHER INFORMATION: primer DNAJC24-2-R

<400> SEQUENCE: 82
cttttgattc ctgctttgat                                            20

<210> SEQ ID NO 83
<211> LENGTH: 19
<212> TYPE: DNA
<213> ORGANISM: Artificial Sequence
<220> FEATURE:
<223> OTHER INFORMATION: primer DNAJC24-3-F

<400> SEQUENCE: 83
```

```
cccttctgct ttgtccatc                                                    19

<210> SEQ ID NO 84
<211> LENGTH: 20
<212> TYPE: DNA
<213> ORGANISM: Artificial Sequence
<220> FEATURE:
<223> OTHER INFORMATION: primer DNAJC24-3-R

<400> SEQUENCE: 84
accacatttc tgggttgctc                                                   20

<210> SEQ ID NO 85
<211> LENGTH: 20
<212> TYPE: DNA
<213> ORGANISM: Artificial Sequence
<220> FEATURE:
<223> OTHER INFORMATION: primer DNAJC24-4-F

<400> SEQUENCE: 85
ggagactttt ggcctagtgt                                                   20

<210> SEQ ID NO 86
<211> LENGTH: 20
<212> TYPE: DNA
<213> ORGANISM: Artificial Sequence
<220> FEATURE:
<223> OTHER INFORMATION: primer DNAJC24-4-R

<400> SEQUENCE: 86
ataaagtttt caggtgggaa                                                   20

<210> SEQ ID NO 87
<211> LENGTH: 20
<212> TYPE: DNA
<213> ORGANISM: Artificial Sequence
<220> FEATURE:
<223> OTHER INFORMATION: primer DNAJC24-5-F

<400> SEQUENCE: 87
taaataaatt cccacctgaa                                                   20

<210> SEQ ID NO 88
<211> LENGTH: 20
<212> TYPE: DNA
<213> ORGANISM: Artificial Sequence
<220> FEATURE:
<223> OTHER INFORMATION: primer DNAJC24-5-R

<400> SEQUENCE: 88
acaatagcca tgttttctga                                                   20

<210> SEQ ID NO 89
<211> LENGTH: 20
<212> TYPE: DNA
<213> ORGANISM: Artificial Sequence
<220> FEATURE:
<223> OTHER INFORMATION: primer DNAJC24-6-F

<400> SEQUENCE: 89
ggcaactgta gaaaggatag                                                   20

<210> SEQ ID NO 90
<211> LENGTH: 20
<212> TYPE: DNA
<213> ORGANISM: Artificial Sequence
```

```
<220> FEATURE:
<223> OTHER INFORMATION: primer DNAJC24-6-R

<400> SEQUENCE: 90
tataaagaat aagcaccaca                                                    20

<210> SEQ ID NO 91
<211> LENGTH: 23
<212> TYPE: DNA
<213> ORGANISM: Artificial Sequence
<220> FEATURE:
<223> OTHER INFORMATION: primer DNAJC24-7-F

<400> SEQUENCE: 91
tggtatttat tattggtttg gac                                                23

<210> SEQ ID NO 92
<211> LENGTH: 20
<212> TYPE: DNA
<213> ORGANISM: Artificial Sequence
<220> FEATURE:
<223> OTHER INFORMATION: primer DNAJC24-7-R

<400> SEQUENCE: 92
aggagaaagg gatgacaagg                                                    20

<210> SEQ ID NO 93
<211> LENGTH: 19
<212> TYPE: DNA
<213> ORGANISM: Artificial Sequence
<220> FEATURE:
<223> OTHER INFORMATION: primer DNAJC27-1-F

<400> SEQUENCE: 93
ctcctccagt tccctaccc                                                     19

<210> SEQ ID NO 94
<211> LENGTH: 21
<212> TYPE: DNA
<213> ORGANISM: Artificial Sequence
<220> FEATURE:
<223> OTHER INFORMATION: primer DNAJC27-1-R

<400> SEQUENCE: 94
acagcccagt aagttatcag c                                                  21

<210> SEQ ID NO 95
<211> LENGTH: 22
<212> TYPE: DNA
<213> ORGANISM: Artificial Sequence
<220> FEATURE:
<223> OTHER INFORMATION: primer DNAJC27-2-F

<400> SEQUENCE: 95
ttgaaaacat acccatattt gg                                                 22

<210> SEQ ID NO 96
<211> LENGTH: 20
<212> TYPE: DNA
<213> ORGANISM: Artificial Sequence
<220> FEATURE:
<223> OTHER INFORMATION: primer DNAJC27-2-R

<400> SEQUENCE: 96
atcactaaaa ggaagctctc                                                    20
```

```
<210> SEQ ID NO 97
<211> LENGTH: 22
<212> TYPE: DNA
<213> ORGANISM: Artificial Sequence
<220> FEATURE:
<223> OTHER INFORMATION: primer DNAJC27-3-F

<400> SEQUENCE: 97
cttcatcttg ctcctactgt cc                                              22

<210> SEQ ID NO 98
<211> LENGTH: 21
<212> TYPE: DNA
<213> ORGANISM: Artificial Sequence
<220> FEATURE:
<223> OTHER INFORMATION: primer DNAJC27-3-R

<400> SEQUENCE: 98
caaagggttg gttcacttct g                                               21

<210> SEQ ID NO 99
<211> LENGTH: 18
<212> TYPE: DNA
<213> ORGANISM: Artificial Sequence
<220> FEATURE:
<223> OTHER INFORMATION: primer DNAJC27-4-F

<400> SEQUENCE: 99
agggacaggg tagaaggc                                                   18

<210> SEQ ID NO 100
<211> LENGTH: 18
<212> TYPE: DNA
<213> ORGANISM: Artificial Sequence
<220> FEATURE:
<223> OTHER INFORMATION: primer DNAJC27-4-R

<400> SEQUENCE: 100
caaacatggc accagaaa                                                   18

<210> SEQ ID NO 101
<211> LENGTH: 18
<212> TYPE: DNA
<213> ORGANISM: Artificial Sequence
<220> FEATURE:
<223> OTHER INFORMATION: primer DNAJC27-5-F

<400> SEQUENCE: 101
ggcaaacgtg atgaagcc                                                   18

<210> SEQ ID NO 102
<211> LENGTH: 18
<212> TYPE: DNA
<213> ORGANISM: Artificial Sequence
<220> FEATURE:
<223> OTHER INFORMATION: primer DNAJC27-5-R

<400> SEQUENCE: 102
gacctggagc ccagcaat                                                   18

<210> SEQ ID NO 103
<211> LENGTH: 22
<212> TYPE: DNA
<213> ORGANISM: Artificial Sequence
<220> FEATURE:
<223> OTHER INFORMATION: primer DNAJC27-6-F
```

<400> SEQUENCE: 103
agagtaggat cataagccat tt    22

<210> SEQ ID NO 104
<211> LENGTH: 20
<212> TYPE: DNA
<213> ORGANISM: Artificial Sequence
<220> FEATURE:
<223> OTHER INFORMATION: primer DNAJC27-6-R

<400> SEQUENCE: 104
ttcggtgaag gagtagtgtt    20

<210> SEQ ID NO 105
<211> LENGTH: 20
<212> TYPE: DNA
<213> ORGANISM: Artificial Sequence
<220> FEATURE:
<223> OTHER INFORMATION: primer DNAJC27-7-F

<400> SEQUENCE: 105
tgcaagaggt gttctgttat    20

<210> SEQ ID NO 106
<211> LENGTH: 20
<212> TYPE: DNA
<213> ORGANISM: Artificial Sequence
<220> FEATURE:
<223> OTHER INFORMATION: primer DNAJC27-7-R

<400> SEQUENCE: 106
tttcaggggt tctactatgt    20

<210> SEQ ID NO 107
<211> LENGTH: 22
<212> TYPE: DNA
<213> ORGANISM: Artificial Sequence
<220> FEATURE:
<223> OTHER INFORMATION: primer DNAJC27-8-F

<400> SEQUENCE: 107
acatagtaga acccctgaaa gt    22

<210> SEQ ID NO 108
<211> LENGTH: 20
<212> TYPE: DNA
<213> ORGANISM: Artificial Sequence
<220> FEATURE:
<223> OTHER INFORMATION: primer DNAJC27-8-R

<400> SEQUENCE: 108
atgatgctgc aacaaggaaa    20

<210> SEQ ID NO 109
<211> LENGTH: 20
<212> TYPE: DNA
<213> ORGANISM: Artificial Sequence
<220> FEATURE:
<223> OTHER INFORMATION: primer DNAJC27-9-F

<400> SEQUENCE: 109
tgccaagaca ggtgggaaat    20

<210> SEQ ID NO 110

<211> LENGTH: 20
<212> TYPE: DNA
<213> ORGANISM: Artificial Sequence
<220> FEATURE:
<223> OTHER INFORMATION: primer DNAJC27-9-R

<400> SEQUENCE: 110
caggtagggt aaggcgaatg          20

<210> SEQ ID NO 111
<211> LENGTH: 20
<212> TYPE: DNA
<213> ORGANISM: Artificial Sequence
<220> FEATURE:
<223> OTHER INFORMATION: primer DNAJC27-10-F

<400> SEQUENCE: 111
attcgcctta ccctacctga          20

<210> SEQ ID NO 112
<211> LENGTH: 22
<212> TYPE: DNA
<213> ORGANISM: Artificial Sequence
<220> FEATURE:
<223> OTHER INFORMATION: primer DNAJC27-10-R

<400> SEQUENCE: 112
ctgggaactg agcaagacct aa          22

<210> SEQ ID NO 113
<211> LENGTH: 20
<212> TYPE: DNA
<213> ORGANISM: Artificial Sequence
<220> FEATURE:
<223> OTHER INFORMATION: primer DNAJC27-11-F

<400> SEQUENCE: 113
cttaggtctt gctcagttcc          20

<210> SEQ ID NO 114
<211> LENGTH: 20
<212> TYPE: DNA
<213> ORGANISM: Artificial Sequence
<220> FEATURE:
<223> OTHER INFORMATION: primer DNAJC27-11-R

<400> SEQUENCE: 114
cacaacatct ccaagtccag          20

<210> SEQ ID NO 115
<211> LENGTH: 20
<212> TYPE: DNA
<213> ORGANISM: Artificial Sequence
<220> FEATURE:
<223> OTHER INFORMATION: primer DNAJC27-12-F

<400> SEQUENCE: 115
acttggagat gttgtgctgc          20

<210> SEQ ID NO 116
<211> LENGTH: 20
<212> TYPE: DNA
<213> ORGANISM: Artificial Sequence
<220> FEATURE:
<223> OTHER INFORMATION: primer DNAJC27-12-R

<400> SEQUENCE: 116

```
tatgaacccc tcttcccttt                                              20

<210> SEQ ID NO 117
<211> LENGTH: 21
<212> TYPE: DNA
<213> ORGANISM: Artificial Sequence
<220> FEATURE:
<223> OTHER INFORMATION: primer DNAJC27-13-F

<400> SEQUENCE: 117
gtgtcagtat ctgtcccta a                                             21

<210> SEQ ID NO 118
<211> LENGTH: 20
<212> TYPE: DNA
<213> ORGANISM: Artificial Sequence
<220> FEATURE:
<223> OTHER INFORMATION: primer DNAJC27-13-R

<400> SEQUENCE: 118
tctatgatct cagtcggtaa                                              20
```

METHODS AND COMPOSITIONS FOR IMPROVED FERTILIZATION AND EMBRYONIC SURVIVAL

CROSS REFERENCE TO RELATED APPLICATIONS

This is a divisional application of U.S. application Ser. No. 13/563,750 filed on Aug. 1, 2012 claiming priority to U.S. Patent Application No. 61/514,030, filed on Aug. 2, 2011, the entire disclosure of which is incorporated herein by reference.

STATEMENT OF GOVERNMENT INTEREST

This invention was made with government support under 09-CRHF-0-6055 awarded by the USDA/NIFA. The government has certain rights in the invention.

FIELD OF THE INVENTION

The present invention relates to a method of genetic testing for improved fertilization rate and embryonic survival rate in animals, especially dairy cattle, based on single nucleotide polymorphisms (SNPs) in genes encoding the heat shock proteins (HSP).

BACKGROUND OF THE INVENTION

Poor reproductive performance, in particular in high-producing dairy cows, is a major problem on dairy farms throughout the world and has been identified as the single most important problem in dairy herd management in many countries (Royal et al., 2000; Dobson et al., 2008). In addition to direct financial losses, infertility can result in increased management complexity, for example, an inability to achieve a compact calving pattern, which is of critical importance in maximizing milk production from grazed grass in seasonal production systems.

This is of particular interest in cattle because of declining fertility over the past few decades (Dobson et al., 2007; Leroy et al., 2008). Furthermore, recent studies have shown that low fertilization rates and embryonic loss seem to be the main factors in dairy cattle infertility (Santos et al., 2004; Morris and Diskin, 2008).

While reproductive performance is influenced by a large number of factors, low fertilization rate and early embryonic loss are the primary factors contributing to poor reproductive performance in dairy cattle (Santos et al., 2004; Morris and Diskin, 2008). Enormous efforts, such as animal breeding and artificial insemination, have been and continue to be invested in ensuring adequate fertility in the cattle herd. Typically, artificial insemination in dairy cattle is successful only 30-35% of the time. The reasons for this are not clear. However, it is understood that both biological and environmental factors affect fertility rate. Some environmental factors such as high temperature, and lack of precipitation can cause stress in cattle and can drop the fertility rate to 10-15%. Commercial artificial insemination operations often shut down in July and August due to the drop in fertility caused by the hot, dry weather.

Genetics is also a prominent factor in fertility, and accounts for about one-third of the decline in pregnancy rate of dairy cows (Shook, 2006). In particular, identifying highly fertile bulls has been a time-consuming and expensive process. It can take 5-10 years of tracking the attempts of artificial insemination using semen from a bull before it can be certified as a quality bull.

Marker-assisted selection, on the other hand, can lower the high cost and reduce the extended time commitment of progeny testing currently used to improve sires, since young bull progeny could be evaluated immediately after birth or even prior to birth for the presence/absence of the marker, and young bulls that are determined by genetic testing to have undesirable markers would never be progeny tested.

There is thus a need for a method of genetically evaluating the bulls, as well as the cows, e.g., by genetic testing, to enable a quick and accurate evaluation of its fertility as well as the survival rate of embryos conceived therefrom.

Heat shock proteins (HSPs) are among the most highly conserved proteins in nature and have been found in all organisms studied from bacteria to humans (Becker and Craig, 1994). The structure and roles of HSPs as molecular chaperones in the folding, transport, and assembly of proteins as well as in protecting the cell under different stress conditions have been extensively studied and reported in the scientific literature (Becker and Craig, 1994; Nollen and Morimoto, 2002; Qiu et al., 2006). The fact that HSPs are essential in the folding, stability, and cellular localization of newly synthesized proteins implies key roles of these proteins in apoptosis, cell differentiation, and regulation of the embryo cell cycle (Luft and Dix, 1999; Lanneau et al., 2007). Strong evidence which has accumulated on the expression of HSPs during spermatogenesis, oogenesis, and embryogenesis suggests they have important functions in fertilization and during the pre-implantation period (Neuer et al., 1999). Mouse embryos cultured with monoclonal antibodies to HSPs have been found to display a significantly reduced blastocyst rate (Neuer et al., 1998). Al-Katanani and Hansen (2002) reported that the addition of antibodies for the induced form of HSP70 reduced blastocyst rate of cattle embryos, suggesting that HSP70 is involved in proper embryonic development. Matwee and colleagues (2001) showed that fertilization—measured as the number of permatozoa tightly bound to a zona pellucida—and embryo development in cattle were significantly affected by the presence of different concentrations of anti-HSP70.

Although there is strong evidence in the literature on the roles of HSPs in early embryonic development, most of the studies have focused on the mouse and only a few HSP genes have been studied in cattle embryos. No evidence existed that any polymorphism in HSPs, if existed, is related to dairy cattle fertility in any way.

SUMMARY OF THE INVENTION

The present inventor investigated the expression profiles of HSPs and their splice variants in bovine embryos (degenerates vs. blastocysts), and also analyzed the association of these profiles with fertility traits. Some splice variants showed differential expression between degenerates and blastocysts while others were not expressed at all in embryos, implying different functions of these transcripts in embryonic development. Among the HSPs investigated, DNAJC15, DNAJC19, DNAJC24 and DNAJC27, all of the HSP40 family, had the most significant expression differential. They were further investigated for association with fertility and development traits. Single nucleotide polymorphisms (SNP) in DNAJC15 and DNAJC27 were found to be associated with blastocyst rate and fertilization rate, respectively.

Accordingly, the present invention provides an isolated nucleic acid molecule comprising at least one polymorphic site selected from the group consisting of positions 85146, 85161, 85216, 85292, and 85300 of the nucleic acid sequence shown in FIG. 1 (SEQ ID NO: 1) (part of the DNAJC15 gene), and at least 10 contiguous nucleotides of the sequence shown in FIG. 1, wherein position 85146 is guanine, position 85161 is guanine, position 85216 is adenosine, position 85292 is cytosine, or position 85300 is guanine; or an isolated nucleic acid molecule comprising a polymorphic position selected from the group consisting of positions 35728, 36016, and 38867 of the nucleic acid sequence shown in FIG. 2 (SEQ ID NO: 2) (part of the DNAJC27 gene), and at least 10 contiguous nucleotides of the sequence shown in FIG. 2, wherein position 35728 is guanine, position 36016 is guanine, or position 38867 is guanine. It is recognized that SEQ ID NO: 1 is already known, and the nucleic acid molecule therefore does not encompass one that consists of SEQ ID NO: 1.

Preferably, the nucleic acid molecule which comprises at least 15, more preferably at least 20, still more preferably at least 25, contiguous bases of SEQ ID NO: 1 or SEQ ID NO: 2 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

In another embodiment, the nucleic acid molecule contains the polymorphic site which is at the 5'-end of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting single nucleotide polymorphism (SNP) in the bovine DNAJC15 or DNAJC27 genes, wherein the DNAJC15 gene is partially shown in FIG. 1, and the DNAJC27 gene is partially shown in FIG. 2, the method comprising optionally isolating a nucleic acid sample from the bovine animal or a tissue sample therefrom, determining the identity of a nucleotide of at least one position selected from the group consisting of a first polymorphic position comprising positions 85146, 85161, 85216, 85292, and 85300 of SEQ ID NO: 1, and a second polymorphic position comprising positions 35728, 36016, and 38867 of SEQ ID NO: 2, and comparing the nucleotide identity of the position respectively to the nucleotide identity at a corresponding position of SEQ ID NO: 1 or SEQ ID NO: 2.

Also provided is a method for genotyping a bovine cell, comprising obtaining a nucleic acid sample from said cell and determining the identity of a nucleotide of at least one position selected from the group consisting of positions 85146, 85161, 85216, 85292, and 85300 of SEQ ID NO: 1, and positions 35728, 36016, and 38867 of SEQ ID NO: 2. In one embodiment, the bovine cell is an adult cell, an embryo cell, a sperm, an egg, a fertilized egg, or a zygote. In one embodiment, both copies of the gene in the cell are genotyped.

The present invention further provides a method for progeny testing of cattle, the method comprising collecting a nucleic acid sample from said progeny, and genotyping said nucleic sample.

In another embodiment, a method is provided for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo, and terminating pregnancy if the developing embryo does not have at least one polymorph selected from the group consisting of a first polymorph selected from the group consisting of guanine at position 85146, guanine at position 85161, adenosine at position 85216, cytosine at position 85292, guanine at position 85300 of SEQ ID NO: 1; and a second polymorph selected from the group consisting of guanine at position 35728, guanine at position 36016, and guanine at position 38867 of SEQ ID NO: 2.

In one embodiment, pregnancy is terminated if the developing embryo does not have either the first polymorph or the second polymorph.

In another embodiment, pregnancy is terminated if the developing embryo is not homozygous in the first polymorph and the second polymorph.

Further provided is a method for selecting a cattle as a breeder, wherein the cattle is genotyped according to the present invention, and the animal is only selected for breeding purpose if it comprises at least a first polymorph or a second polymorph, wherein the first polymorph is selected from guanine at position 85146, guanine at position 85161, adenosine at position 85216, cytosine at position 85292, guanine at position 85300 of SEQ ID NO: 1; and the second polymorph is selected from the group consisting of guanine at position 35728, guanine at position 36016, and guanine at position 38867 of SEQ ID NO: 2. In one embodiment, the cattle animal is selected only if it comprises both the first and second polymorphs. In another embodiment, the cattle animal is selected only if it is homozygous with regard to both the first and second polymorphs.

DESCRIPTION OF THE DRAWINGS

FIG. 1 shows a portion of the DNAJC15 gene sequence (SEQ ID NO: 1) where the polymorphic sites and some of the PCR primers are shown. The five polymorphic sites are highlighted.

FIG. 2 shows a portion of the DNAJC27 gene sequence (SEQ ID NO: 2) where the polymorphic sites and some of the PCR primers are shown. The three polymorphic sites are highlighted, bold faced and underlined.

Black boxes represent coding sequences and white boxes represent untranslated regions. Due to overlap for DNAJB12, only transcript DNAB12-1220 could be amplified using transcript-specific primers.

Figure 5:
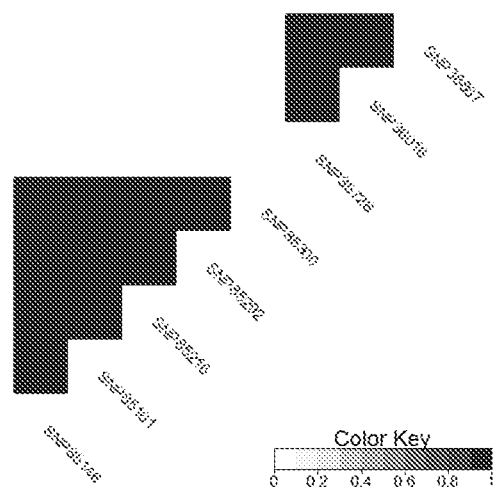

FIG. 5 is a heat map of linkage disequilibrium ($r^2$) between SNPs in DNAJC15 and DNAJC27. SNPs 85146, 85161, 85216, 85292 and 85300 are located in DNAJC15 while SNPs 35728, 36016 and 38867 are located in DNAJC27.

DETAILED DESCRIPTION OF THE INVENTION

The present inventor has constructed an in-vitro fertilization (IVF) system which has the advantages of a unified environment and well-isolated components of the embryonic development process, and used this system to characterize genetic factors involved in embryonic loss, and hence infertility, and to associate candidate genes and pathways with fertilization rate and embryonic survival at both the genomic and gene expression levels (Khatib et al., 2008a,b; Khatib et al., 2009; Huang et al., 2010a,b).

As indicated above, HSPs are among the first proteins produced during embryonic development (Neuer et al., 1999). The present inventor hypothesized that determining expression patterns of these genes in developed vs. arrested embryos could lead to the identification of specific genes involved in reproductive success. The high structural and functional conservation of HSPs during evolution suggests crucial roles of these proteins in fertilization, embryo development, and thus fertility in cattle. Also, some HSPs are considered housekeeping genes that are essential for many cell functions.

In efforts leading to the present invention, the expression levels of HSP genes in biological replicate bovine embryo pools that differ in their morphology and developmental statuses were evaluated, and associations of polymorphisms with fertility traits were examined. The HSP genes were found to be differentially expressed between blastocysts and degenerate embryos.

SNPs in two HSP genes were found to be associated with fertility traits. Specifically, a total of 17 candidate genes were chosen based on differential expression results observed in a previous microarray analysis of bovine embryos. To test whether or not these genes have roles in early development of cattle embryos, their expression levels were quantified and compared between blastocysts and degenerates. All 17 genes showed expression differences that ranged between 1.5- and 7.6-fold between the embryo groups. Two of these bovine HSP genes, DNAJC15 and DNAJC27, both of the HSP40 gene family, have several polymorphic positions, and these polymorphisms are associated with fertilization and blastocyst rates. Furthermore, all SNPs in each of DNAJC15 and DNAJC27 genes showed high linkage disequilibrium with each other.

The term "polymorphic" or "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the genotypes of the two HSP genes, which are found to have strong correlation to fertilization rate and embryonic survival.

The provided sequences also encompass the complementary sequence corresponding to any of the provided polymorphisms. In order to provide an unambiguous identification of the specific site of a polymorphism, the numbering of the original sequence in the GenBank is shown in FIG. 1 and is used throughout this disclosure.

The present invention provides nucleic acid based genetic markers for identifying bovine animals with superior breeding (such as fertility and embryo survival rates) traits. In general, for use as markers, nucleic acid fragments, preferably DNA fragments, may be as short as 7 nucleotides (nt), but may preferably be at least 12 nt, 15 nt, usually at least 20 nt, often at least 50 nt. Such small DNA fragments are useful as primers for the polymerase chain reaction (PCR), and/or probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with the template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridizing to a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is SNP genotyping, that is, to determine which embodiment of the SNP polymorphisms a specific sample of DNA has. For example, it is desirable to determine whether the nucleotide at a particular position is A or C. Many references describe genotyping methods, such as Chen et al., "Single nucleotide polymorphism genotyping: biochemistry, protocol, cost and throughput", Pharmacogenomics J. 2003; 3(2):77-96; Kwok et al., "Detection of single nucleotide polymorphisms", Curr Issues Mol. Biol. April 2003; 5(2):43-60; Shi, "Technologies for individual genotyping: detection of genetic polymorphisms in drug targets and disease genes", Am J. Pharmacogenomics. 2002; 2(3):197-205; and Kwok, "Methods for genotyping single nucleotide polymorphisms", Annu Rev Genomics Hum Genet. 2001; 2:235-58. Exemplary techniques for high-throughput SNP genotyping are described in Marnellos, "High-throughput SNP analysis for genetic association studies", Curr Opin Drug Discov Devel. May 2003; 6(3):317-21. Common SNP genotyping methods include, but are not limited to, TaqMan assays and modifications thereof such as Molecular Beacon assays, SNPlex platforms, Bio-Plex system, CEQ and SNPstream systems, Molecular Inversion Probe array technology, BeadArray Technologies (e.g., Illumina GoldenGate and Infinium assays), single stranded conformation polymorphism assays (SSCP), molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

The sequence neighboring the SNP site can be used to design SNP detection reagents such as oligonucleotide probes, which may optionally be implemented in a kit format. Preferably, the oligonucleotide probe will have a detectable label, and contains for example an A at the corresponding position. Experimental conditions can be chosen such that if the sample DNA contains an A, a hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the target gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of a SNP position may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis discussed above (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the target gene of the sample of interest may be amplified via PCR and directly sequenced, and the sequence be compared to the wild type sequence. It is readily recognized that, other than those specifically disclosed herein, numerous primers can be devised to achieve the objectives. PCR and sequencing techniques are well known in the art and reagents and equipments are readily available commercially.

The so-called next generation sequencing, and high-throughput sequencing methods, may also be sued. For example, Massively Parallel Signature Sequencing (MPSS); Polony sequencing, pyro sequencing, SOLiD sequencing; ion semiconductor sequencing, and DNA nanoball sequencing systems are well-known to those skilled in the art.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a sample is collected from the individual animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved fertilization rate and embryonic survival.

Further provided is a method for genotyping the bovine HSP gene, comprising determining for the two copies of the HSP gene present the identity of the nucleotide pair at positions 25402 and 19069.

One embodiment of a genotyping method of the invention involves examining both copies of the relevant HSP gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

Testing of Roles of 17 HSP Genes

The roles of 17 HSP genes in early embryonic development and fertility in cattle at both genomic and gene expression levels were investigated. These genes include 8 HSP40 genes, six HSP70 genes, one HSPP, and 2 HSP10 genes. (see Table 1) These genes were chosen based on differential expression results observed in a previous microarray analysis of bovine embryos; and their expression levels were quantified and compared between blastocysts and degenerates to test whether or not these genes have roles in early development of cattle embryos.

All 17 genes showed expression differences that ranged between 1.5- and 7.6-fold between the embryo groups. All HSP40 family genes were found to be upregulated in degenerate embryos compared to blastocysts. Although the specific functions of HSP40s have not been reported in cattle, studies from other species have shown that these genes play important roles in protecting cells under stress conditions (Lanneau et al., 2007). It is well established that ATP hydrolysis is necessary for protein folding activity of HSP70s and that HSP40s stimulate ATPase activity and stabilize the interaction of HSP70s with their substrates (Qiu et al., 2006). Gotoh and colleagues (2004) reported that HSP40 combines with HSP70 to act as chaperones to protect cells from apoptosis. Degenerate embryos in the IVF system are growth-arrested embryos and seem to undergo partial apoptosis. Research has shown that HSPs are upregulated to prevent apoptosis triggered by different stimuli by interacting with key factors of the apoptotic signaling pathways (Lanneau et al., 2007). Therefore, it is feasible that upregulation of HSP40 genes observed in degenerates is a response to stress on these embryos so they can maintain protein homeostasis.

The qRT-PCR analysis revealed moderate fold change expression of HSPE1, HSPH1, HSB1, and six HSP70 genes (HSPA2, HSPA4, HSPA5, HSPA8, HSPA9 and HSPA14). HSPA2, HSPA4, HSPA5, and HSPA8 showed higher expression in blastocysts than degenerates, whereas expression levels of HSPA9 and HSPA14 were higher in degenerate embryos. Although the specific functions of most HSP70s have not been reported in cattle, studies in human and mouse have indicated important roles for these genes in early embryogenesis. It has been reported that Hspa2 is essential for normal spermatogenesis and for growth and survival of cancer cells and that Hspa8 knockout mice are not viable because of the housekeeping functions of this gene (Daugaard et al., 2007). Human HSPA5 is involved in the folding and transport of proteins into the endoplasmic reticulum and Hspa5 knockout mice embryos die at day 3.5, and therefore it, too, is considered a housekeeping gene (Daugaard et al., 2007). Furthermore, Matwee et al. (2001) have reported a reduced blastocyst rate and an increased apoptosis of embryos cultured in the presence of anti-HSP70.

Thus, upregulation and downregulation of HSPs in bovine embryos observed in the present study imply that these genes play vital roles in early embryo development.

Given that alternative splicing is a major source of phenotypic complexity in mammals (Wang et al., 2008), a search was conducted of the Ensembl annotation of the bovine genome and found that only 4 out of 17 HSP candidate genes have annotated splice variants. In contrast, for the 17 human and mouse counterparts, 15 and 13 genes, respectively, have 2 or more splice variants. The low number of alternative transcripts identified in cattle is presumably due to the incomplete annotation of the bovine genome. Indeed, in a previous study, thousands of alternative splicing events were characterized in blastocysts and degenerative embryos, and some of those events were found to be associated with the developmental status of embryos (Huang and Khatib, 2010).

In order to explore the effects of the different splice variants of HSPs on embryo development, expression levels of the identified variants were estimated and compared between blastocysts and degenerate embryos. The results clearly show that different splice variants display different expression levels which imply different functions in embryo development. For example, while the long variant of DNAJC24 was highly expressed in degenerate embryos compared to blastocysts, the short variant of this gene was found to be lowly expressed in both embryo groups. Also, for DNAJC5, one transcript could not be detected using qRT-PCR. These results are consistent with human studies in which only some of the splice variants of genes were found to be associated with a disease state (Wang and Cooper, 2007). Collectively, these results testify to the importance of alternative splicing as a key regulator of phenotypic variation in mammals.

To better understand the involvement of the HSP genes in fertility traits, 4 genes that showed the most significant expression differences between embryo groups were tested for SNP association.

Recently, an IVF experimental system in cattle has been developed in our laboratory (see Methods) aimed at identifying genetic factors affecting fertilization and embryo development. The effectiveness of this system in identifying genes and pathways associated with developmental and fertility traits has been demonstrated in several studies (Khatib et al., 2008a,b; Khatib et al., 2009; Driver et al., 2009; Wang et al., 2009; Huang et al., 2010a).

Analysis of DNAJC15 and DNAJC27 SNP revealed significant associations with blastocyst and fertilization rates, respectively. These results are of particular significance because these 2 genes showed a remarkable difference in expression between blastocysts and degenerate embryos, providing strong evidence for the involvement of these genes in embryo production and development in cattle. The results also provide further evidence for the roles of HSPs in the fertilization process and blastocyst rates observed in mice and cattle in previous studies. Neuer et al. (1998) found that the presence of anti-HSP60 monoclonal antibodies had significant effects on blastocyst rates of mouse embryos. Matwee et al. (2001) reported that the addition of anti-HSP70 monoclonal antibodies to the culture medium reduced the mean number of spermatozoa bound to zona pellucida by about 50% to that of controls. Also, the authors reported that anti-HSP70 significantly reduced the number of bovine embryos that reached the blastocyst stage (Matwee et al., 2001). A recent study by Rosenkrans et al. (2010) reported an association between SNP in the promoter region of HSP70 and calving percentages in Brahman cows. Although a small sample size was used in the association analysis, the results point to an important role of HSP70 in cow fertility.

The identification of specific HSP genes contributing to embryo survival can be a unique opportunity to improve protection of IVF embryos from different toxic conditions and to enhance pregnancy rates in cattle (Hansen, 2007). HSP genes investigated in this study were found to be differentially expressed between blastocysts and degenerate embryos and SNP in 2 genes were associated with fertility traits. Blastocysts and degenerate embryos have distinct morphological and developmental features. As such, the present study provides a set of candidate genetic markers for pre-implantation embryo development. However, it has been reported that relatively small changes (decrease or increase) in expression levels of heat shock proteins can result in growth abnormalities and cell death (Nollen and Morimoto, 2002). Also, the assessment of the expression of alternative transcript isoforms in the embryos examined in this study testifies to the importance of inclusion of this approach in studying gene expression.

The present invention accordingly provides novel cattle genotyping, selective cattle breeding and related methods, based on the discovery that certain HSP40 polymorphism confers improved fertilization and embryonic survival rate to cattle.

The following examples are intended to illustrate preferred embodiments of the invention and should not be interpreted to limit the scope of the invention as defined in the claims.

EXAMPLES

Materials and Methods
  In-Vitro Maturation, Fertilization, and Embryo Culture
  In this study, fertilization and embryo production were performed in 2 different experiments. The first experiment is a comparison of expression profiles of 17 HSPs between 2 populations of embryos differing in their morphology, and the second experiment is a genomic association analysis of genes—found to be differentially-expressed in the first experiment—with fertilization and blastocyst rates.
  Experiment I: Expression Analysis of HSP Genes in Cattle Embryos
  Ovaries were obtained from a local abattoir and processed for IVF using standard protocol (Huang et al., 2010b; Khatib et al., 2008a). Briefly, oocytes were aspirated from 2-6 mm follicles and washed in Tyrode's albumin lactate pyruvate (TALP)-Hepes after which they underwent maturation in supplemented M199 media (Khatib et al., 2008a). Incubation was completed at 5% $CO_2$ in air at 39° C. and high humidity for 22-24 hours at which time oocytes were then washed in TALP-Hepes and moved into fresh IVF-TALP (Biowhittaker, Walkersburg, Md.). Semen samples from 2 different bulls were used for fertilization; sperm underwent Percoll separation (45-90% gradient) and were adjusted to a final concentration of $1 \times 10^6$/ml (Parrish et al., 1995). Fertilization was marked as day 0 of development and completed by combining sperm, heparin, and PHE with the oocytes in 44 μl drops of media (Khatib et al., 2008a). Incubation was then continued for 22-24 hours after which the putative zygotes were washed in TALP-Hepes, denuded of remaining cumulus cell complexes, and placed into supplemented synthetic oviductal fluid (Biowhittaker) and returned to incubation (Khatib et al., 2008a).
  Morphological Assessment
  Putative zygotes were cultured over an 8-day period during which assessments of their developmental progress were made. By day 5 of development, a bovine embryo should attain approximately 16-32 cells and show signs of cellular compaction deeming it as morula. Embryos failing to show these characteristics were assumed to have been arrested in development and were excluded from analysis. Morulas were then continued in culture until day 8. By this time an embryo should show evidence of a fluid filled cavity (blastocoele), which gives rise to the differentiation of the inner cell mass and the trophectoderm, qualifying it as a blastocyst. For expression analysis, there were 2 populations of embryos collected. The first consisted of embryos that attained a compacted morula status by day 5 but failed to form a blastocoele by day 8, referred as degenerate embryos. The second consisted of embryos that developed into blastocysts by day 8. Embryos from each morphological group were collected in pools of 20 and preserved in RNALater (Ambion, Austin, Tex.). Two bulls were used with 2 sets of biological replicate pools (total of 4 biological replicates) from each to prevent maternal crossover.
  Quantitative Real-Time PCR (qRT-PCR)
  A previous study in our laboratory using microarray expression analysis has revealed that many genes are differentially expressed between blastocysts and degenerate embryos (Huang et al., 2010b). Seventeen HSP genes that showed 1.5-fold or higher differences in expression between the embryo groups described in the study of Huang et al. (2010b) were chosen for validation of differential expression and further investigation in new sets of blastocysts and degenerate embryo pools using qRT-PCR analysis. Primers (Table 1) were designed to amplify fragments spanning more than one exon to exclude the possibility of genomic DNA contamination in the qRT-PCR reactions using the Beacon Designer software (Premier Biosoft International, Palo Alto, Calif.). Total RNA was extracted from pools of embryos using RNaqueous Micro (Ambion) and quality controlled using a RNA6000 PicoChip (Agilent Technologies, CA). Messenger RNA was amplified using MessageAmp II (Ambion, Austin, Tex.), followed by cDNA synthesis using iScript (Bio-Rad, Hercules, Calif.) according to manufacturers' instructions. Reactions of qRT-PCR were run on a DNA Engine—Opticon 2 Detection System (MJ Research, Watertown, Mass.) using iQ SYBR Green Supermix kit (Bio-Rad Laboratories, CA). Each sample was run in quadruplicate and all 4 expression results were averaged. Analysis of gene expression levels was conducted using the $2^{-\Delta\Delta Ct}$ method (Livak and Schmittgen, 2001). The selection of the housekeeping gene GAPDH as an endogenous control was as described in Huang et al. (2010b).
  Experiment II: Association Analysis of Differentially-Expressed HSPs with Fertilization and Blastocyst Rates
  In order to further investigate the involvement in fertility of genes (DNAJC15, DNAJC19, DNAJC24, and DNAJC27) that showed the highest fold change in expression in degenerate embryos vs. blastocysts, an association analysis between SNPs in these genes and 2 main fertility traits: fertilization rate and blastocyst rate was performed. Using the IVF experimental system, several genes were found to be significantly associated with variation in fertilization and embryonic survival rates (Khatib et al., 2008a,b; Khatib et al., 2009).
  Phenotypic Data. In order to generate phenotypic data for association analysis, a total of 6,893 in-vitro fertilizations were performed using oocytes from 399 ovaries (obtained from 399 Holstein cows) and semen samples from 12 Holstein bulls. For 92 ovaries, oocytes were fertilized by two different bulls each. Fertilization rate was calculated as the number of cleaved embryos 48 h postfertilization out of the total number of oocytes exposed to sperm. Blastocyst rate was calculated as the number of embryos that reached blastocyst stage out of the total embryos cultured by day 8. asdf Genotyping. DNA was extracted from ovaries (n=399) using standard phenol/chloroform protocols. The DNA concentrations were measured using a spectrophotometer (Ultraspec 2100; Amersham Biosciences). For polymorphism identification, 3 DNA pools were constructed from 20 different ovary/cow samples to contain 25 ng of DNA from each sample. DNA Pools were amplified with different sets of primers designed from the coding and 5' and 3' UTR regions of the 4 candidate genes (Table 3). Amplification, sequencing of PCR products, and SNP identification were as described in Khatib et al. (2008a,b). SNP identified in DNAJC15, DNAJC19, DNAJC24, and DNAJC27 were genotyped for the 399 ovary/cow samples at GeneSeek (Lincoln, Nebr.).

Statistical Analysis

For expression analysis, normalized gene expression values ($\Delta Ct$) were analyzed using a general linear model including the fixed effects of the bull, the type of embryo (blastocyst or degenerate), and the random effect of the pool. Association between the normalized gene expression and the type of embryo was tested using a likelihood ratio test by comparing this model to a reduced model without the embryo effect. The mean and the range of the fold change for each gene were calculated as $2^{-\Delta\Delta Ct}$ using the estimated $\Delta\Delta Ct$ value±standard error.

For genomic association analysis between SNP and fertilization and blastocyst rates, the following mixed linear model was used, $$y_{ijk} = \mu + o_i + b_j + SNP_{ijk} + e_{ijk}$$

where $y_{ijk}$ represents in turn, the fertilization or survival rate of oocytes k from ovary i fertilized with semen from bull j; $\mu$ represents a general mean for the trait considered, $o_i$ represents the random effect of the individual ovary from which oocytes were harvested; $b_j$ represents the random effect of the sire used in the fertilization; $SNP_{ijk}$ represents the fixed effect of the genotypic class for the SNP considered; and $e_{ijk}$ represents the residuals, assumed normal, independent and identically distributed with mean 0 an variance $I\sigma_e^2$. Ovaries and bulls were assumed uncorrelated with variance structures $I\sigma_o^2$ and $I\sigma_b^2$, respectively. Association between the SNP and fertilization or blastocyst rates was tested using a likelihood ratio test by comparing the full model to a reduced model without the SNP effect. All analyses were performed using the lme4 package of R language/environment (R Development Core Team, 2009).

Results

Expression Profiling of HSP Genes in Embryos

Expression differences between degenerate embryos and blastocysts were estimated for 17 HSP genes in 4 sets of biological replicates using qRT-PCR (FIG. 1). A range of 1.5- to 7.6-fold difference in expression was observed between embryo groups. Interestingly, all HSP40 gene family members were found to be upregulated in degenerate embryos compared to blastocysts (FIG. 1). For example, DNAJC15 (P<0.0001), DNAJC19 (P<0.0001), DNAJC24 (P=0.002), and DNAJC27 (P=0.0098) showed an average of 7.6-, 4.8-, 3.3-, 4.33-fold differences in expression, respectively. In contrast, only 2 members of HSP70 family (HSPA14 and HSPA9) showed upregulation in degenerates, whereas 4 HSP70 genes (HSPA2, HSPA4, HSPA5, and HSPA8) showed higher expression levels in blastocysts than in degenerates (FIG. 1).

Differential Expression of Alternatively-Spliced Transcripts

Splice variants of HSP genes were identified using the genebuild procedure of Ensembl (http://uswest.ensembl.org/). In this procedure, annotation of transcripts is based on mRNA and protein sequences deposited in public scientific databases. Ensembl search revealed one transcript per gene for 13 genes, 2 transcripts each for DNAJB12 and DNAJC19, and 3 transcripts each for DNAJC5 and DNAJC24. Expression levels of splice variants of DNAJC5, DNAJC19, DNAJC24, and DNAJB12 (FIG. 2) were estimated in 4 sets of biological replicates of blastocysts and degenerate embryos using qRT-PCR. Transcripts DNAJC5-1049 and DNAJC5-667 (FIG. 2) showed 2.53- and 1.67-fold higher expression, respectively, in degenerate embryos compared to blastocysts while the DNAJC5-725 transcript was not detected in any of the embryo groups. For DNAJC19, only transcript DNAJC19-536 was detected in embryos. For DNAJC24, DNAJC24-2172 transcript showed a 3.22-fold higher expression in degenerate embryos compared to blastocysts, whereas transcript DNAJC24-628 was lowly expressed in all embryo samples. DNAJC24-1893 transcript could not be detected in embryos. The sequences of the 2 DNAJB12 transcripts were overlapping so that only transcript DNAB12-1220 could be amplified using transcript-specific primers. DNAB12-1220 showed a 1.95-fold higher expression in degenerate embryos vs. blastocysts.

Association of HSP Polymorphisms with Fertilization and Blastocyst Rates

Figure 3:
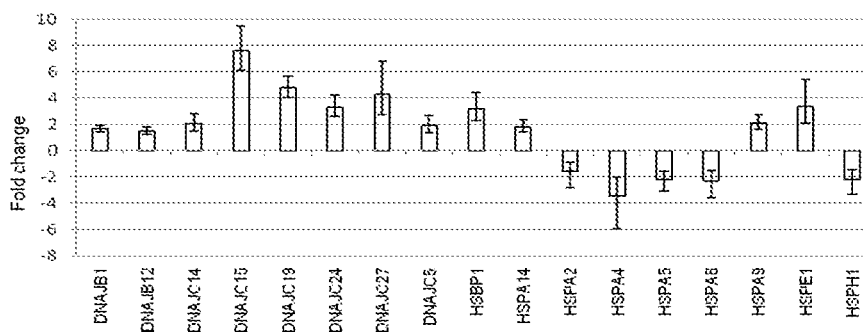
FIG. 3 shows the changes in expression levels of heat shock protein genes in bovine embryos using qRT-PCR. Data are shown as mean+/−maximum and minimum fold changes. Upregulation in degenerate or blastocyst embryos is represented by bars above or below, respectively, the x axis. qRT-PCR was performed in 4 sets of biological replicates of blastocysts and degenerate embryos.
Figure 4:
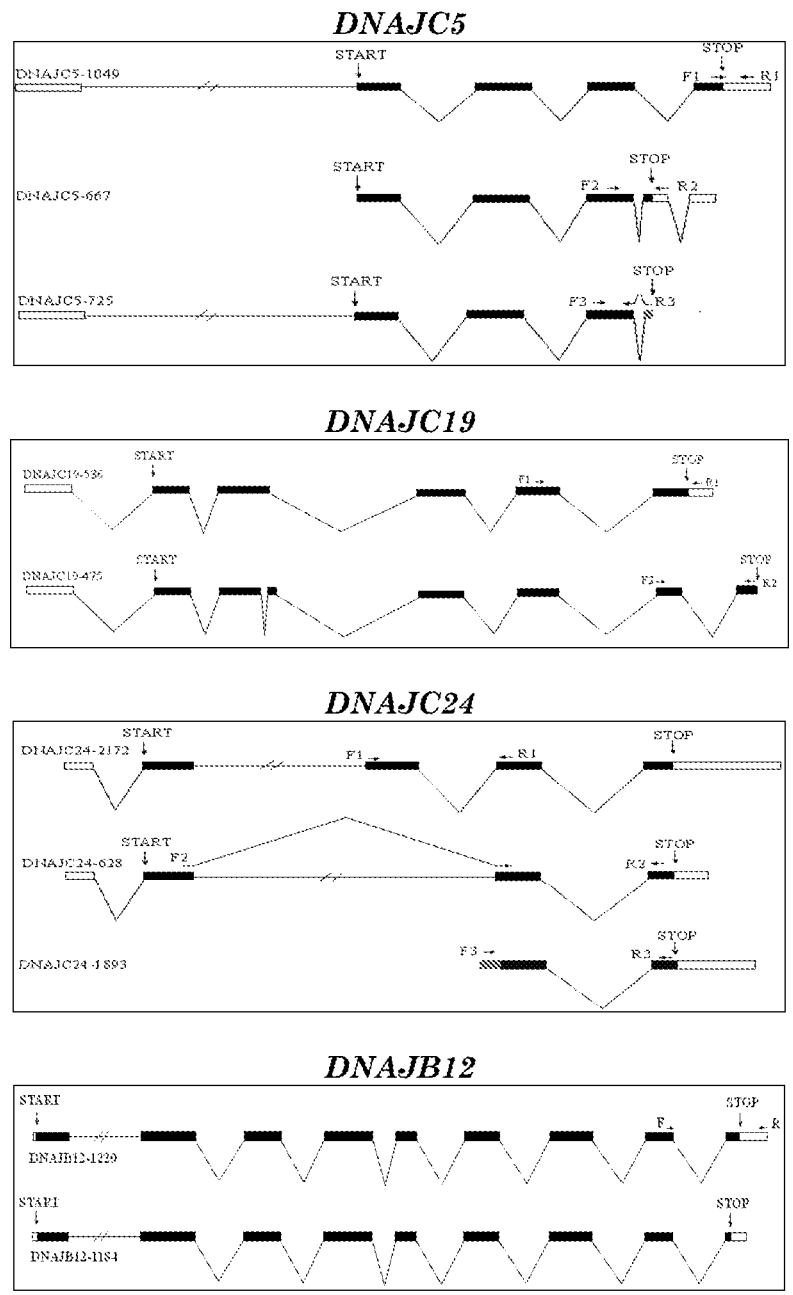
FIG. 4 shows the splice variants of DNAJC5, DNAJC19, DNAJC24, and DNAJB12 genes. Positions of start and stop codons are indicated by vertical arrows and positions of primers used in the qRT-PCR are indicted by horizontal arrows.

SNP in genes DNAJC15, DNAJC19, DNAJC24, and DNAJC27 were tested for association with fertilization and blastocyst rates. These genes showed the highest fold differences in expression between embryo groups (FIG. 1) and the highest statistical significance in the general linear model analysis (P<0.01). Using the pooled DNA sequencing approach, 5 SNP were identified in the 3'UTR of DNAJC15, one SNP in exon 5 of DNAJC19, one SNP and one 4-bp deletion in the 3' UTR of DNAJC24, and 3 SNP in the 3' UTR of DNAJC27. All SNP in each of DNAJC15 and DNAJC27 genes showed high linkage disequilibrium with each other (FIG. 3). Polymorphisms in DNAJC19 and DNAJC24 did not show significant associations with fertility traits. Table 2 shows fertilization and blastocysts rates for the genotypic classes of the DNAJC15 and DNAJC27 SNP. For DNAJC27 SNP36016, oocytes collected from genotype GG ovaries showed a 69.3% fertilization rate vs. 62.2% for oocytes collected from CC ovaries (P=0.034). For DNAJC15 SNP85146, the blastocyst rate of embryos produced from GG dams was 40.1% vs. 31.0% and 28.1% for embryos produced from AA and AG dams, respectively (Table 2).

While the invention has been described in connection with one or more embodiments, it should be understood that the invention is not limited to those embodiments, and the description is intended to cover all alternatives, modifications, and equivalents, as may be included within the spirit and scope of the appended claims. All referenced cited herein are further incorporated by reference in their entirety.

REFERENCES CITED

Becker, J., and E. A. Craig. 1994. Heat-shock proteins as molecular chaperones. Eur. J. Biochem. 219:11-23.

Carlborg, O., and C. S. Haley. 2004. Epistasis: too often neglected in complex trait studies? Nat. Rev. Genet. 5:618-625.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.

Darnell, J. E. 1997. STATs and gene regulation. Science 277:1630-1635.

Daugaard, M., M. Rohde, and M. Jäättelä. 2007. The heat shock protein 70 family: Highly homologous proteins with overlapping and distinct functions. FEBS Lett. 581:3702-3710.

Dobson, H., R. Smith, M. Royal, Ch. Knight, and I. Sheldon. 2007. The high-producing dairy cow and its reproductive performance. Reprod Domest Anim. 42 Suppl 2:17-23.

Dobson, H., S. L. Walker, M. J. Morris, J. E. Routly, and R. F. Smith. 2008. Why is it getting more difficult to successfully artificially inseminate dairy cows? Animal 2:1104-1111.

Driver, A. M., W. Huang, S. Gajic, R. L. Monson, G. J. Rosa, and H. Khatib. 2009. Effects of the progesterone receptor variants on fertility traits in cattle. J. Dairy Sci. 92:4082-4085.

Hansen, P. J. 2007. To be or not to be—determinants of embryonic survival following heat shock. Theriogenology 68 Suppl 1:S40-8.

Hombría, J. C., and S. Brown. 2002. The fertile field of Drosophila Jak/STAT signalling. Curr. Biol. 12:R569-R575.

Huang, W., B. W. Kirkpatrick, G. J. Rosa, and H. Khatib. 2010a. A genome-wide association study using selective DNA pooling identifies candidate markers for fertility in Holstein cattle. Anim. Genet. 41:570-578.

Huang, W., B. S. Yandell, and H. Khatib. 2010b. Transcriptomic profiling of bovine IVF embryos revealed candidate genes and pathways involved in early embryonic development. BMC Genomics 11:23.

Huang, W., and H. Khatib. 2010. Comparison of transcriptomic landscapes of bovine embryos using RNA-Seq. BMC Genomics 11:711.

Kisseleva, T., S. Bhattacharya, J. Braunstein and C. W. Schindler. 2002. Signaling through the JAK/STAT pathway, recent advances and future challenges. Gene 285:1-24.

Khatib, H., R. L. Monson, V. Schutzkus, D. M. Kohl, G. J. Rosa, and J. J. Rutledge. 2008a. Mutations in the STAT5A gene are associated with embryonic survival and milk composition in cattle. J. Dairy Sci. 91:784-793.

Khatib, H., C. Maltecca, R. L. Monson, V. Schutzkus, X. Wang, and J. J. Rutledge. 2008b. The fibroblast growth factor 2 gene is associated with embryonic mortality in cattle. J. Anim. Sci. 86:2063-2067.

Khatib, H., W. Huang, X. Wang, A. H. Tran, A. B. Bindrim, V. Schutzkus, R. L. Monson, and B. S. Yandell. 2009. Single gene and gene interaction effects on fertilization and embryonic survival rates in cattle. J. Dairy Sci. 92:2238-2247.

Kodama, H., K. Fukuda, J. Pan, S. Makino, A. Baba, S. Hori, and S. Ogawa. 1997. Leukemia inhibitory factor, a potent cardiac hypertrophic cytokine, activates the JAK/STAT pathway in rat cardiomyocytes. Circ. Res. 81:656-663.

Lanneau, D., A. de Thonel, S. Maurel, C. Didelot, and C. Garrido. 2007. Apoptosis versus cell differentiation: role of heat shock proteins HSP90, HSP70 and HSP27. Prion 1:53-60.

Leroy, J. L., G. Opsomer, A. Van Soom, I. G. Goovaerts, and P. E. Bols. 2008. Reduced fertility in high-yielding dairy cows: are the oocyte and embryo in danger? Part I. The importance of negative energy balance and altered corpus luteum function to the reduction of oocyte and embryo quality in high-yielding dairy cows. Reprod Domest Anim. 43:612-622.

Livak, K. J., and T. D. Schmittgen. 2001. Analysis of relative gene expression data using real-time quantitative PCR and the 2(-Delta Delta C(T)) Method. Methods 25:402-408.

Luft, J. C., and D. J. Dix. 1999. Hsp70 expression and function during embryogenesis. Cell Stress Chaperones 4:162-170.

Maj, T., and A. Chelmonska-Soyta. 2007. Pleiotropy and redundancy of STAT proteins in early pregnancy. Reprod. Domest. Anim. 42:343-353.

McCullagh, P., and J. A. Nelder. 1989. Generalized Linear Models, 2nd edn. Chapman and Hall, London.

Morris, D., and M. Diskin. 2008. Effect of progesterone on embryo survival. Animal 2:1112-1119.

Neuer, A., C. Mele, H. C. Liu, Z. Rosenwaks, and S. S. Witkin. 1998. Monoclonal antibodies to mammalian heat shock proteins impair mouse embryo development in vitro. Hum. Reprod. 13:987-990.

Neuer, A., S. D. Spandorfer, P. Giraldo, J. Jeremias, S. Dieterle, I. Korneeva, H. C. Liu, Z. Rosenwaks, and S. S. Witkin. 1999. Heat shock protein expression during gametogenesis and embryogenesis. Infect. Dis. Obstet. Gynecol. 7:10-6.

Nollen, E. A., and R. I. Morimoto. 2002. Chaperoning signaling pathways: molecular chaperones as stress-sensing 'heat shock' proteins. J. Cell Sci. 115:2809-2816.

Parrish, J. J., A. Krogenaes, and J. L. Susko-Parrish. 1995. Effect of bovine sperm separation by either swim-up or Percoll method on success of in vitro fertilization and early embryonic development. Theriogenology 44:859-869.

Qiu, X. B., Y. M. Shao, S. Miao, and L. Wang. 2006. The diversity of the DnaJ/Hsp40 family, the crucial partners for Hsp70 chaperones. Cell Mol. Life. Sci. 63:2560-2570.

R Development Core Team. 2008. R: A Language and Environment for Statistical Computing. R Foundation for Statistical Computing, Vienna, Austria. (www.R-project.org).

Royal, M., G. E. Mann, and A. P. Flint. 2000. Strategies for reversing the trend towards subfertility in dairy cattle. Vet. J. 160:53-60.

Santos, J. E. P., W. W. Thatcher, R. C. Chebel, R. L. A. Cerri, and K. N. Galvao. 2004. The effect of embryonic death rates in cattle on the efficacy of estrus synchronization programs. Anim. Reprod. Sci. 83:513-535.

Shook G. E. 2006. Major advances in determining appropriate selection goals. J. Dairy Sci. 89:1349-1361.

Soller, M. (1990) Genetic mapping of the bovine genome using DNA-level markers with particular attention to loci affecting quantitative traits of economic importance. J. Dairy Sci. 73:2628-2646.

Soller, M. (1994) Marker-assisted selection, an overview. Anim. Biotech. 5:193-208.

Takeda, K., K. Noguchi, W. Shi, T. Tanaka, M. Matsumoto, N. Yoshida, T. Kishimoto, and S. Akira. 1997. Targeted disruption of the mouse Stat3 gene leads to early embryonic lethality. Proc. Natl. Acad. Sci. USA. 94:3801-3804.

Teglund, S., C. McKay, E. Schuetz, J. M. van Deursen, D. Stravopodis, D. Wang, M. Brown, S. Bodner, G. Grosveld and J. N. Ihle. 1998. Stat5a and Stat5b proteins have essential and nonessential, or redundant, roles in cytokine responses. Cell 93:841-850.

Truchet, S., M. Chebrout, C. Djediat, J. Wietzerbin, and P. Debey. 2004. Presence of permanently activated signal transducers and activators of transcription in nuclear interchromatin granules of unstimulated mouse oocytes and preimplantation embryos. Biol. Reprod. 71:1330-1339.

VanRaden, P. M., A. H. Sanders, M. E. Tooker, R. H. Miller, H. D. Norman, M. T. Kuhn, and G. R. Wiggans. 2004. Development of a national genetic evaluation for cow fertility. J. Dairy Sci. 87:2285-2292.

Wang, G. S., and T. A. Cooper. 2007. Splicing in disease: disruption of the splicing code and the decoding machinery. Nat. Rev. Genet. 8:749-761.

Wang, X., V. Schutzkus, W. Huang, G. J. Rosa, and H. Khatib. 2009. Analysis of segregation distortion and association of the bovine FGF2 with fertilization rate and early embryonic survival. Anim. Genet. 40:722-728.

Wang, E. T., R. Sandberg, S. Luo, I. Khrebtukova, L. Zhang, C. Mayr, S. F. Kingsmore, G. P. Schroth, and C. B. Burge. 2008. Alternative isoform regulation in human tissue transcriptomes. Nature 456:470-476.

TABLE 1

Primers for total expression and alternative splicing analyses of HSP genes

| | Family | forward primer 5'-3' | reverse primer 5'-3' | amplicon size (bp) |
|---|---|---|---|---|
| Gene | | | | |
| GAPDH | | TGCCCAGAATATCATCCC (SEQ ID NO: 3) | AGGTCAGATCCACAACAG (SEQ ID NO: 4) | 134 |
| DNAJC5 | HSP40 | CTACGACAAGTACGGCTCAC (SEQ ID NO: 5) | GGCAGCAGCAACAGTAGC (SEQ ID NO: 6) | 149 |
| DNAJC15 | HSP40 | AGGTCGCTACGCATTTCAG (SEQ ID NO: 7) | GACTTGCTTCTCGCCTACTC (SEQ ID NO: 8) | 137 |
| DNAJC19 | HSP40 | GGACTGACCATTGCTGCTG (SEQ ID NO: 9) | CAAACCCACCTCTGTAATAGC (SEQ ID NO: 10) | 140 |
| DNAJC24 | HSP40 | GAAATATGGGACCAGTAGATGC (SEQ ID NO: 11) | TGTAACTTCTTCTGCTTCATCC (SEQ ID NO: 12) | 134 |
| DNAJC27 | HSP40 | AACAAGCGGACACCATTCG (SEQ ID NO: 13) | TGAAGCAGCACAGCAAGC (SEQ ID NO: 14) | 124 |
| HSPA5 | HSP70 | CAACCAACTGTTACCATCAAGG (SEQ ID NO: 15) | AAAGGTGACTTCAATCTGTGG (SEQ ID NO: 16) | 133 |
| HSPA9 | HSP70 | GACCAACTGCCTGCTGATG (SEQ ID NO: 17) | GATGCCGCCTGCCTTATG (SEQ ID NO: 18) | 113 |
| HSPA8 | HSC70 | CGCAGAAGCCTACCTTGG (SEQ ID NO: 19) | GTTGAGACCAGCAATAGTTCC (SEQ ID NO: 20) | 115 |
| HSPA14 | HSP70 | AACCTTAGCACAGTACCTAGC (SEQ ID NO: 21) | TGTCAGCACCGTTCATCAG (SEQ ID NO: 22) | 101 |
| HSBP1 | HSBP | CATGTCCGACCAGATCATTG (SEQ ID NO: 23) | TTCACTGTCCAGCTCTTCC (SEQ ID NO: 24) | 115 |
| HSPE1 | HSP10 | GCAAGCAACGGTGGTAGC (SEQ ID NO: 25) | ACTTTGGTGCCTCCATATTCTG (SEQ ID NO: 26) | 117 |
| DNAJB1 | HSP40 | GAGGAGAAGTTCAAGGAGATCG (SEQ ID NO: 27) | TTAGTACCGCCGCTGCTC (SEQ ID NO: 28) | 134 |
| DNAJB12 | HSP40 | GCAAACTAGCCCTCAAATTCC (SEQ ID NO: 29) | CCTTGTCATCACCGAACTGG (SEQ ID NO: 30) | 141 |
| DNAJC14 | HSP40 | GTGAATGAGTTTCTGTCCAAGC (SEQ ID NO: 31) | GTATCTGGCACTCTTAGGTTCC (SEQ ID NO: 32) | 114 |
| HSPA2 | HSP70 | ACGCTGTGGAGTCCTATACC (SEQ ID NO: 33) | TTCCGCCATCTGGTTCCG (SEQ ID NO: 34) | 146 |
| HSPA4 | HSP70 | TCCTGCCTTAGAAGAGAAACC (SEQ ID NO: 35) | CCCAGTGTTGTGTCAAATGC (SEQ ID NO: 36) | 132 |
| HSPH1 | HSP100 | ATGTTGAGTTGCCTATTGAAGC (SEQ ID NO: 37) | CCTCCACCGCATTCTTAGC (SEQ ID NO: 38) | 141 |
| Transcript | | | | |
| DNAJC5-667 | | AGGAGACGGAGTTCTATG (SEQ ID NO: 39) | CACGTTCACACCTCAAC (SEQ ID NO: 40) | 126 |
| DNAJC5-725 | | GGCCCTGTTCATCTTCTG (SEQ ID NO: 41) | GGCACAGACCCTCTCAT (SEQ ID NO: 42) | 181 |
| DNAJC5-1049 | | GGGTTCAACTAAATCCAGGA (SEQ ID NO: 43) | ACGCCATCTCTGTGACTA (SEQ ID NO: 44) | 79 |
| DNAJC19-475 | | GGATCTCCTTATATAGCAGCCAAA (SEQ ID NO: 45) | AGCCTTCCCTCCCAGTGA (SEQ ID NO: 46) | 93 |
| DNAJC19-536 | | ATGCTCATCGGCGAATTATG (SEQ ID NO: 47) | AGCTGGAACGCATAAGAGAA (SEQ ID NO: 48) | 161 |
| DNAJC24-628 | | CTCATTTTAATGGAAGATG (SEQ ID NO: 49) | GTATCACAAGAAATCAGT (SEQ ID NO: 50) | 176 |
| DNAJC24-2172 | | CATCCAGATAAACAGAGT (SEQ ID NO: 51) | GGTCCCATATTTCTTAGAT (SEQ ID NO: 52) | 161 |
| DNAJC24-1893 | | CAAAAGAAAGTATCTCATTC (SEQ ID NO: 53) | TAACTTCTTCTGCTTCATC (SEQ ID NO: 54) | 176 |
| DNAJB12-1220 | | ACCGACTGTCAGAGACTATG (SEQ ID NO: 55) | CGGCCTCCAATTCCATTT (SEQ ID NO: 56) | 127 |

TABLE 2

Blastocyst and fertilization rates for genotypic classes of DNAJC15 and DNAJC27 genes

| DNAJC15 SNP | genotype (number of ovaries) | blastocyst rate ± SE | P value |
|---|---|---|---|
| SNP 85146(G > A) | AA (202) | 0.310 ± 0.025 | 0.014 |
| | AG (206) | 0.281 ± 0.025 | |
| | GG (53) | 0.401 ± 0.040 | |

TABLE 2-continued

Blastocyst and fertilization rates for genotypic classes of DNAJC15 and DNAJC27 genes

| | | | |
|---|---|---|---|
| SNP 85161(G > A) | AA (202) | 0.309 ± 0.023 | 0.022 |
| | AG (206) | 0.283 ± 0.024 | |
| | GG (61) | 0.390 ± 0.037 | |
| SNP 85216(A > G) | GG (203) | 0.312 ± 0.022 | 0.059 |
| | AG (201) | 0.282 ± 0.023 | |
| | AA (63) | 0.373 ± 0.036 | |
| SNP 85292(C > A) | AA (204) | 0.310 ± 0.023 | 0.012 |
| | AC (201) | 0.279 ± 0.024 | |
| | CC (62) | 0.395 ± 0.037 | |
| SNP 85300(G > A) | AA (208) | 0.312 ± 0.023 | 0.066 |
| | AG (201) | 0.280 ± 0.023 | |
| | GG (63) | 0.369 ± 0.037 | |

| DNAJC27 SNP | genotype (number of ovaries) | fertilization rate ± SE | P value |
|---|---|---|---|
| SNP 35728(G > A) | AA (126) | 0.621 ± 0.029 | 0.042 |
| | AG (257) | 0.654 ± 0.025 | |
| | GG (103) | 0.691 ± 0.030 | |
| SNP 36016(C > G) | CC (129) | 0.622 ± 0.029 | 0.034 |
| | CG (251) | 0.653 ± 0.026 | |
| | GG (103) | 0.693 ± 0.030 | |
| SNP 38867(A > G) | AA (133) | 0.626 ± 0.028 | 0.049 |
| | AG (246) | 0.650 ± 0.026 | |
| | GG (104) | 0.693 ± 0.030 | |

TABLE 3

Primers used for SNP identification, product sizes, and GenBank accession numbers of amplified genes

| Primer | Primer sequence (5'-3') | Amplicon (bp) | GenBank Accession no. |
|---|---|---|---|
| DNAJC15-1 | F: CCGGAGGTCTGCAAA TGGG (SEQ ID NO: 57) R: AACTGCTCGCCTGGTG CTGGTC (SEQ ID NO: 58) | 589 | NC_007310 |
| DNAJC15-2 | F: TCACTGAAAATCAGC CAATA (SEQ ID NO: 59) R: CGTACAGAAGAGCCCCAT (SEQ ID NO: 60) | 569 | NC_007310 |
| DNAJC15-3 | F: AATTGCTTTATTACTT TAGCGG (SEQ ID NO: 61) R: AGGGACCATGTCTGT TTTGT (SEQ ID NO: 62) | 647 | NC_007310 |
| DNAJC15-4 | F: AAAGTCCCTGTAGAGCT TAG (SEQ ID NO: 63) R: ATAAAGGCACATCACAA CTA (SEQ ID NO: 64) | 571 | NC_007310 |
| DNAJC15-5 | F: TCCTCCTGTCCTAGT TCTTG (SEQ ID NO: 65) R: TTCATTATGCCCAAA TCAGT (SEQ ID NO: 66) | 647 | NC_007310 |
| DNAJC15-6 | F: CCATCCACTTCAGAA AATTC (SEQ ID NO: 67) | 620 | NC_007310 |
| | R: GGGGAAAGATCAGTGC TAGAGT (SEQ ID NO: 68) | | |
| DNAJC19-1 | F: T TTTCCGACCTAGTTT ACGG (SEQ ID NO: 69) R: ACTTCTACTTCACCAC AGGGA (SEQ ID NO: 70) | 670 | NC_007299 |
| DNAJC19-2 | F: AGCCGCATACCTTTA CAATG (SEQ ID NO: 71) R: ATGGGTCACTTCAGA TTCCT (SEQ ID NO: 72) | 696 | NC_007299 |
| DNAJC19-3 | F: TCCCAGAAGAACTGG GTTTG (SEQ ID NO: 73) R: AGATGGAAGTCCCTG GCAGT (SEQ ID NO: 74) | 496 | NC_007299 |
| DNAJC19-4 | F: TTTAACTCACTGGAG GTAGG (SEQ ID NO: 75) R: ACCAAAACAGCAAGT AGACC (SEQ ID NO: 76) | 597 | NC_007299 |
| DNAJC19-5 | F: AGGGATTGTTGATAA CTGGA (SEQ ID NO: 77) R: TTTATACCAACGCT TTGACT (SEQ ID NO: 78) | 611 | NC_007299 |
| DNAJC24-1 | F: GCTCGGCTGGAAACTTGA (SEQ ID NO: 79) R: CGGTGGATGGCCCTCTAA (SEQ ID NO: 80) | 672 | NC_007313 |
| DNAJC24-2 | F: CCATTTCCTTCTCCA CTAGT (SEQ ID NO: 81) R: CTTTTGATTCCTGCT TTGAT (SEQ ID NO: 82) | 630 | NC_007313 |
| DNAJC24-3 | F: CCCTTCTGCTTTGTCC ATC (SEQ ID NO: 83) R: ACCACATTTCTGGGTTG CTC (SEQ ID NO: 84) | 538 | NC_007313 |
| DNAJC24-4 | F: GGAGACTTTTGGCCTA GTGT (SEQ ID NO: 85) R: ATAAAGTTTTCAGGT GGGAA (SEQ ID NO: 86) | 637 | NC_007313 |
| DNAJC24-5 | F: TAAATAAATTCCCAC CTGAA (SEQ ID NO: 87) R: ACAATAGCCATGTTT TCTGA (SEQ ID NO: 88) | 649 | NC_007313 |

TABLE 3-continued

Primers used for SNP identification, product sizes, and GenBank accession numbers of amplified genes

| Primer | Primer sequence (5'-3') | Amplicon (bp) | GenBank Accession no. |
|---|---|---|---|
| DNAJC24-6 | F: GGCAACTGTAGAAAGG ATAG (SEQ ID NO: 89) R: TATAAAGAATAAGCA CCACA (SEQ ID NO: 90) | 539 | NC_007313 |
| DNAJC24-7 | F: TGGTATTTATTATTGG TTTGGAC (SEQ ID NO: 91) R: AGGAGAAAGGGATGA CAAGG (SEQ ID NO: 92) | 531 | NC_007313 |
| DNAJC27-1 | F: CTCCTCCAGTTCCCT ACCC (SEQ ID NO: 93) R: A CAGCCCAGTAAGTT ATCAGC (SEQ ID NO: 94) | 665 | NC_007309 |
| DNAJC27-2 | F: TTGAAAACATACCCATA TTTGG (SEQ ID NO: 95) R: ATCACTAAAAGGAAG CTCTC (SEQ ID NO: 96) | 682 | NC_007309 |
| DNAJC27-3 | F: CTTCATCTTGCTCCTA CTGTCC (SEQ ID NO: 97) R: CAAAGGGTTGGTTCA CTTCTG (SEQ ID NO: 98) | 647 | NC_007309 |
| DNAJC27-4 | F: AGGGACAGGGTAGAAGGC (SEQ ID NO: 99) R: CAAACATGGCACCAGAAA (SEQ ID NO: 100) | 607 | NC_007309 |
| DNAJC27-5 | F: GGCAAACGTGATGAAGCC (SEQ ID NO: 101) R: GACCTGGAGCCCAGCAAT (SEQ ID NO: 102) | 692 | NC_007309 |
| DNAJC27-6 | F: AGAGTAGGATCATAAGC CATTT (SEQ ID NO: 103) R: TTCGGTGAAGGAGTAG TGTT (SEQ ID NO: 104) | 532 | NC_007309 |
| DNAJC27-7 | F: TGCAAGAGGTGTTCTGT TAT (SEQ ID NO: 105) R: TTTCAGGGGTTCTACT ATGT (SEQ ID NO: 106) | 666 | NC_007309 |
| DNAJC27-8 | F: ACATAGTAGAACCCCTG AAAGT (SEQ ID NO: 107) R: ATGATGCTGCAACAAG GAAA (SEQ ID NO: 108) | 500 | NC_007309 |
| DNAJC27-9 | F: TGCCAAGACAGGTGGG AAAT (SEQ ID NO: 109) R: CAGGTAGGGTAAGGC GAATG (SEQ ID NO: 110) | 613 | NC_007309 |
| DNAJC27-10 | F: ATTCGCCTTACCCTA CCTGA (SEQ ID NO: 111) R: CTGGGAACTGAGCAAG ACCTAA (SEQ ID NO: 112) | 644 | NC_007309 |
| DNAJC27-11 | F: CTTAGGTCTTGCTCAG TTCC (SEQ ID NO: 113) R: CACAACATCTCCAAG TCCAG (SEQ ID NO: 114) | 668 | NC_007309 |
| DNAJC27-12 | F: ACTTGGAGATGTTGTG CTGC (SEQ ID NO: 115) R: TATGAACCCCTCTTC CCTTT (SEQ ID NO: 116) | 565 | NC_007309 |
| DNAJC27-13 | F: GTGTCAGTATCTGTCC CCTAA (SEQ ID NO: 117) R: TCTATGATCTCAGTC GGTAA (SEQ ID NO: 118) | 681 | NC_007309 |

What is claimed is:

1. A method for selectively breeding cattle, the method comprising obtaining fertilized eggs, culturing said fertilized eggs into developing embryos, determining the identity of a nucleotide of HSP gene of the developing embryos corresponding to at least one position selected from the group consisting of positions 1648, 1936, and 4787 of SEQ ID NO: 2, wherein the HSP gene comprises a nucleotide sequence of SEQ ID NO: 2, to identify a developing embryo whose HSP gene comprises guanine at position 1648, 1936, or 4787 of SEQ ID NO: 2, and planting into a suitable female the developing embryo whose HSP gene comprises guanine at position 1648, 1936, or 4787 of SEQ ID NO: 2.

2. The method according to claim 1, wherein a developing embryo whose HSP gene comprises homozygously guanine at position 1648, 1936, or 4787 of SEQ ID NO: 2is identified and planted into a suitable female.

3. A method for selecting a cattle as a breeder, wherein the cattle has a DNAJC15 gene and a DNAJC27 gene, the method comprising:
determining the identity of at least one nucleotide corresponding to a position selected from the group consisting of positions 1326, 1341, 1396, 1472 and 1480 of SEQ ID NO: 1, to identify a cattle whose DNAJC15 gene comprises at least guanine at position 1326, guanine at position 1341, adenosine at position 1396, cytosine at position 1472, or guanine at position 1480 of SEQ ID NO: 1;
determining the identity of at least one nucleotide corresponding to a position selected from the group consisting of positions 1648, 1936 and 4787 of SEQ ID NO: 2, to identify a cattle whose DNAJC27 gene comprises guanine at position 1648, 1936, or 4787 of SEQ ID NO: 2, and
using in a breeding process a cell from the cattle whose DNAJC15 gene comprises guanine at a position corresponding to position 1326 of SEQ ID NO: 1, guanine at a position corresponding to position 1341 of SEQ ID NO: 1, adenosine at a position corresponding to position 1396 of SEQ ID NO: 1, cytosine at a position corresponding to position 1472 of SEQ ID NO: 1, or guanine at a position corresponding to position 1480 of SEQ ID NO: 1, and whose DNAJC27gene comprises guanine at a position corresponding to position 1648, 1936 or 4787 of SEQ ID NO: 2.

4. The method according to claim 3, wherein a cattle animal is identified and selected whose HSP gene comprises homozygously guanine at position 1648, 1936, or 4787 of SEQ ID NO: 2, and gametes from the cattle whose HSP gene homozygously comprises at least guanine at position 1648, guanine at position 1936, or guanine at position 4787 of SEQ ID NO: 2 are used in a breeding process.

5. The method according to claim 3, wherein a bull is selected and its semen used for fertilizing a female animal.

6. The method according to claim 5, wherein a female animal is in vitro fertilized with the semen of the bull.

7. The method according to claim 5, wherein the multiple ovulation and embryo transfer (MOET) procedure is used.

8. The method according to claim 6, wherein said female animal is also homozygous with regard to at least one position selected from the group consisting of positions 1648, 1936 and 4787 of SEQ ID NO: 2.

9. The method according to claim 3, wherein a female animal is selected and is fertilized with semen from a suitable bull.

10. The method according to claim 9, wherein the female animal is in vitro fertilized.

11. The method according to claim 10, wherein MOET procedure is used.

12. A dairy cattle breeding method for improved fertilization or embryo survival rate, the method comprising identifying a cattle the HSP gene of which comprises a nucleotide sequence of SEQ ID NO: 2 and at least guanine at position 1648, guanine at position 1936, or guanine at position 4787 of SEQ ID NO: 2, and using in a breeding process a cell or tissue from the cattle whose HSP gene comprises at least guanine at position 1648, guanine at position 1936, or guanine at position 4787 of SEQ ID NO: 2.

13. The method according to claim 12, wherein the dairy cattle cell is an adult cell, an embryo cell, a sperm, an egg, a fertilized egg, or a zygote.

14. The method according to claim 12, wherein the identity of the nucleotide is determined by sequencing the HSP gene, or a fragment thereof comprising at least one position selected from the group consisting of positions 1648, 1936 and 4787 of SEQ ID NO: 2.

15. The method according to claim 14, wherein the HSP gene or fragment thereof is obtained from the cell or tissue via amplification by the polymerase chain reaction (PCR) of genomic DNA of the cell or tissue.

16. The method according to claim 14, wherein the identity of both copies of the HSP gene is determined.

* * * * *